United States Patent [19]
Chan et al.

[11] Patent Number: 6,037,579
[45] Date of Patent: Mar. 14, 2000

[54] OPTICAL INTERFEROMETER EMPLOYING MULTIPLE DETECTORS TO DETECT SPATIALLY DISTORTED WAVEFRONT IN IMAGING OF SCATTERING MEDIA

[75] Inventors: Kinpui Chan; Koji Satori, both of Yamagata, Japan

[73] Assignee: Biophotonics Information Laboratories, Ltd., Yamagata, Japan

[21] Appl. No.: 09/039,444

[22] Filed: Mar. 16, 1998

[30] Foreign Application Priority Data

Nov. 13, 1997 [JP] Japan .................................. 9-312352

[51] Int. Cl.$^7$ ........................................................ H01J 3/14
[52] U.S. Cl. .......................... 250/216; 250/576; 356/354
[58] Field of Search ................................. 250/216, 575, 250/576, 559.4, 559.39; 356/351, 345, 349, 356, 244, 354, 355

[56] References Cited

U.S. PATENT DOCUMENTS

| | | | |
|---|---|---|---|
| 5,174,298 | 12/1992 | Dolfi et al. ............................ | 128/665 |
| 5,212,667 | 5/1993 | Tomlinson, Jr. et al. .................. | 367/7 |
| 5,491,552 | 2/1996 | Knuttel .................................. | 356/351 |
| 5,493,395 | 2/1996 | Otsuka .................................. | 356/351 |
| 5,883,717 | 3/1999 | DiMarzio et al. ...................... | 356/359 |

FOREIGN PATENT DOCUMENTS

| | | |
|---|---|---|
| 0 193 742 | 9/1986 | United Kingdom . |
| 0 585 620 | 3/1994 | United Kingdom . |

OTHER PUBLICATIONS

"Laser Speckle and Related Phenomena", J.C. Dainty et al., published by Springer–Verlag Co., New York (1975), pp. 9–57, 68–75, (Month Unknown).

"Coherent Detection Techniques in Optical Imaging of Tissues", Kin Pui Chan et al., Physics in Medicine and Biology, vol. 42, 855 (1997), pp. 855–867, Month Unknown.

"Imaging Through Biological Tissues By Use of Optical Low–Coherence Heterodyne Detection Technique", Kin Pui Chan et al., OSA Trends in Optics and Photonics, vol. 2, 250 (1996), pp. 250–255, (Month Unknown).

"Wave Propagation and Scattering in Random Media", Akira Ishimaru, Academic Press (1978), pp. 40–69, (Month Unknown).

"In Vivo Bidirectional Color Doppler Flow Imaging of Picoliter Blood Volumes Using Optical Coherence Tomography", Joseph A. Izatt et al., Opt. Lett. vol. 22 (1997), pp. 1439–1441, Month Unknown.

Andersson–Engels, S et al. "Time–resolved transillumination for medical diagnostics", Nov. 1, 1990, vol. 15 No. 21, *Optics Letters*.

"Experimental Verification of Image Detection in Highly Scattering Media Using Antenna Properties of Optical Heterodyne Microscope Scheme", 24$^{th}$ May 1990, vol. 26, No. 11 pp. 700–701, *Electronics Letters*.

(List continued on next page.)

*Primary Examiner*—Que T. Le
*Attorney, Agent, or Firm*—Oliff & Berridge, PLC

[57] ABSTRACT

There is disclosed an optical measurement device which is based on optical interference and it uses a light beam which is radiated to and transmitted through or reflected by a sample, especially a light scattering medium to optically measure the sample. The amount of signal lights effective for optical heterodyne detection is increased, while speckle noises are averaged out. On an observation plane of a concerned point arranged are plural detector elements. From signals obtained by the respective detector elements, an optical signal of the concerned point is obtained.

15 Claims, 21 Drawing Sheets

OTHER PUBLICATIONS

Chan, K et al. "Coherence gating in optical heterodyne detection measurements of scattering and absorption in highly scattering media", Applied Physics B 63, 249–253 (1996).. (Month Unknown).

Chan, K et al. "Coherent summation of spatially distorted laser Doppler signals by using a two–dimensional heterodyne detector array", *Optics Letters*, vol. 17, No. 17, Sep. 1, 1992, pp. 1237–1239.

Fried, D "Optical Heterodyne Detection of an Atmospherically Distorted Signal Wave Front", *Proceedings of the IEEE*, vol. 55, No. 1, Jan. 1967, pp. 57–67.

Chan, K et al. "Micrometre–resolution, optical imaging of objects through highly scattering media using a heterodyne detector array", $13^{th}$ Oct. 1994, vol. 30, No. 21 pp. 1753–1754, *Electronics Letters*.

T. Wilson, "Confocal Microscopy", Academic Press, London, 1990, pp. 1–64, (Month Unknown).

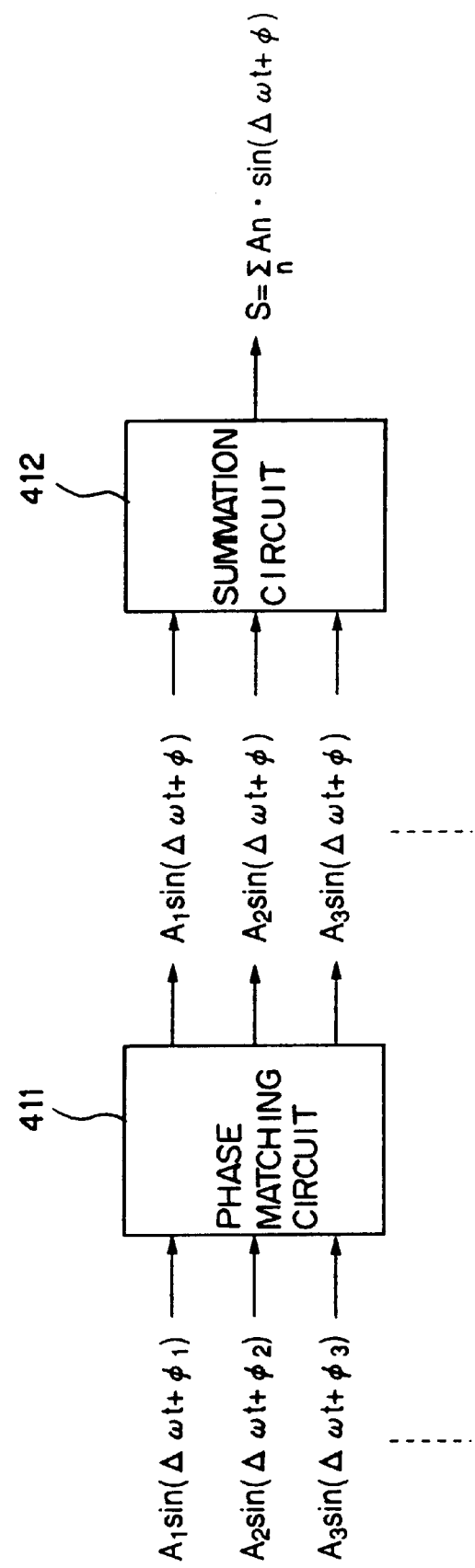

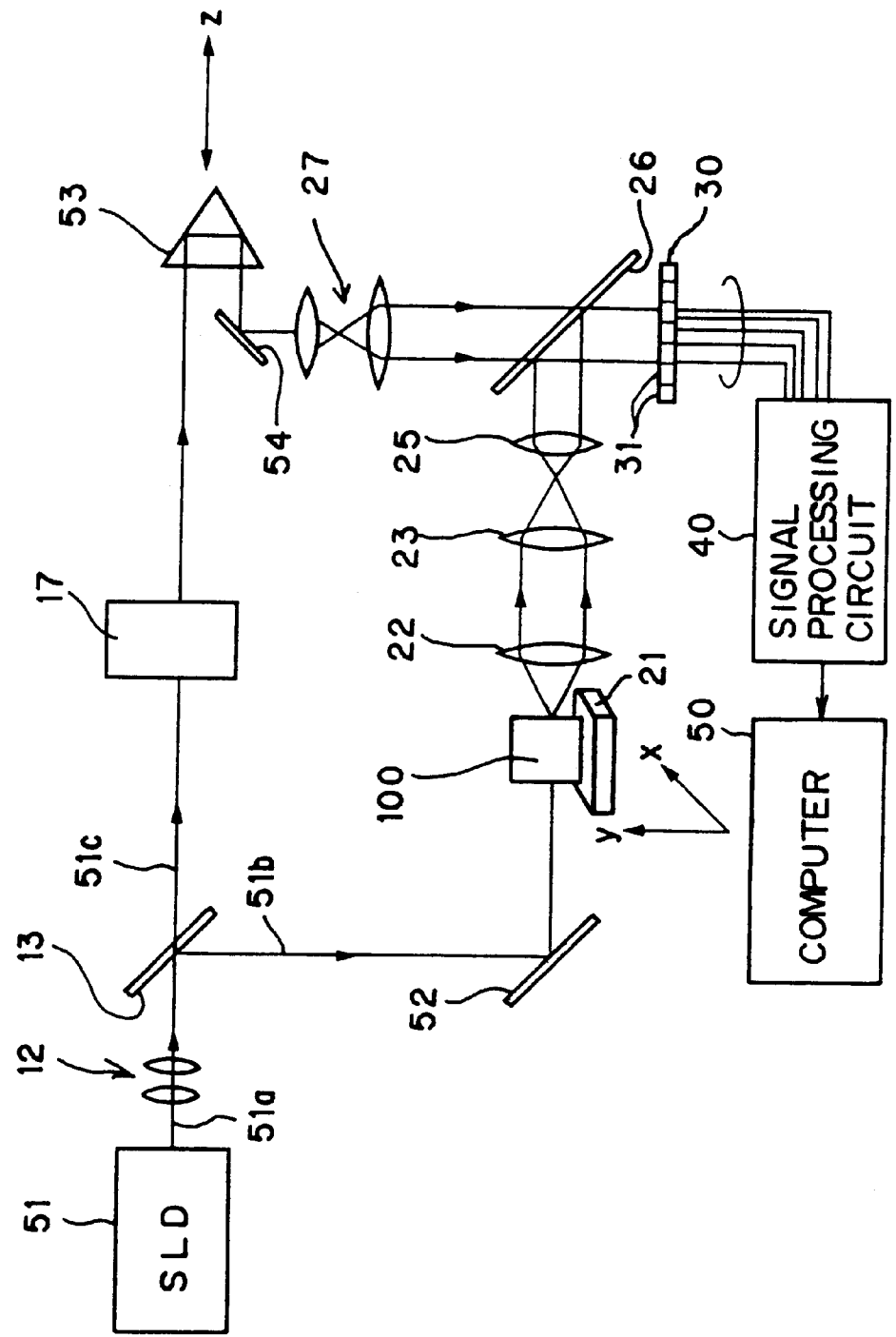

OPTICAL INTERFEROMETER EMPLOYING MULTIPLE DETECTORS TO DETECT SPATIALLY DISTORTED WAVEFRONT IN IMAGING OF SCATTERING MEDIA

BACKGROUND OF THE INVENTION

1. Field of the Invention

The present invention relates to an optical measurement device which uses light beams which are incident upon and transmitted through or reflected by an object, especially a light scattering body, to optically measure the object.

2. Description of the Related Art

The major difficulty of optical measurement of highly scattering media such as, for example, biological systems including human tissues, lies in how to extract the signal light propagated along a traceable optical path from the other transmitted of reflected lights which have been multiply scattered inside the scattering medium. One of the several detection methods is to incident onto the scattering sample an ultra-shot laser pulse having a pulse width of a few picoseconds(picosecond=$10^{-12}$ sec.), and detect the temporal profile of the transmitted laser pulse with an ultra-high speed Streak camera. In this time-resolved detection method, the early arriving photons at the Streak camera appear to travel the shortest distance inside the scattering sample so that they can be regarded as the least-scattered or apparently unscattered light components (refer to, for example, Optics Letters, vol. 15, 1179 (1990) by S. Anderson-Engeles, R. Berg, S. Svanberg, O. Jarlman).

On the other hand, as one of spatially resolved methods, by noting a loss of directional property for the scattered light, there is proposed a method in which an apparently unscattered light component keeping its directional property is detected in an optical heterodyne detection method having a superior direction selectivity which is known as an antenna property (refer to, for example, Electronics Letters, Vol. 26, 700 (1990) by M. Toida, M. Kondo, T. Ichimura, H. Inaba).

FIG. 18 is a principle diagram of the optical heterodyne detection method.

A coherent laser light beam 11a emitted from a laser light source 11 is collimated by using lenses 12 to form a light beam with a predetermined beam diameter, and split by a beam splitter 13 into a signal light 11b and a reference light 11c. The signal light 11b separated from the reference light 11c by the beam splitter 13 is incident upon a sample 100 which is constituted of, for example, a scattering body. The signal light transmitted through the sample 100 is passed via a beam splitter 14 onto a photo detector 15.

On the other hand, the reference light 11c separated from the signal light 11b by the beam splitter 13 is reflected by a mirror 16, then frequency-shifted by an AOM (acousto-optic modulator) or another frequency shifter 17, further reflected by a mirror 18, superimposed on the signal light by the beam splitter 14, and mixed with the signal light on the surface of the photo detector 15. On the photo detector 15 produced is an interference light constituted of the signal light and the reference light which are caused to differ in frequencies from each other by the action of the frequency shifter 17. The output from photo detector 15 consists of a heterodyne signal 15a with a frequency which equals to the frequency difference between the signal light and the reference light.

Optical measurement based on the optical heterodyne detection method detects, intrinsically, in addition to an unscattered light component that advances along the optical axis (on-axis), a near-axis forward scattered light component which, while being multiply scattered inside the sample, retains partially the temporal coherence of the incident light and emerges from the sample in the same direction of the unscattered light. Such a near-axis forward scattered light component exhibits a relatively smaller extinction coefficient as compared with that of the unscattered light, as it has been recently pointed out (refer to Applied Physics B, Vol. 63, 249 (1996) by K. P. Chan, M. Yamada, H. Inaba).

FIG. 19 is given to illustrate an issue in the application of optical heterodyne detection to optical measurement of scattering medium. The performance of heterodyne detection can be adversely affected by light scattering on the exit surface 100a of the sample 100.

The unscattered component and the near-axis forward scattered light component which have been passed though the scattering sample 100 carry information on the internal structure of the sample 100. However, when the exit surface 100a of the sample 100 is not optically flat, i.e., when there exist irregularities in the order of wavelength, light scattering on the exit surface 100a causes the transmitted light spread out rapidly, as it can be explained by the light scattering theory (refer to, for example, "Wave Propagation and Scattering in Random Media", authored by A. Ishimaru and published by Academic Press (1978)). Specifically, following the scattering theory, an outgoing light is scattered and spread out as shown in FIG. 19, for example. In the conventional optical heterodyne method shown in FIG. 18, since a field of view in the optical heterodyne is narrowly restricted ($\theta=\lambda/D$, in which $\lambda$ denotes a wavelength, while D denotes a size of a photo detector), only a part of signal lights emitted from the sample 100 can be detected. Specifically, detected are the signal lights which advance straight in the narrow field of view, i.e., within a remarkably small angle defined by $\theta=\lambda/D$. As a result, the amount of signal light that can be effectively detected by using the heterodyne detection method shown in FIG. 19 can be substantially reduced. Meanwhile, it has been pointed out that in the conventional optical heterodyne method, the light signals spatially distorted by the aforementioned scattering cannot be effectively detected (refer to Optics Letters, Vol. 17, 1237 (1992) by K. P. Chan, D. K. Killinger).

The aforementioned surface scattering not only reduces the amount of signals that can be detected by heterodyne detection, but also induces laser speckle noises. Optical heterodyne detection is based on the interference between the signal light and the reference light. Yet the interference between scattered lights with random phases results in laser speckles, which cause significant fluctuations in the heterodyne signal intensity. Laser speckle is a well known phenomenon (refer to, for example, "Laser Speckle and Related Phenomena", edited by J. C. Dainty and published by Springer-Verlag Co. (New York, 1975)).

FIGS. 20 and 21 are measurement results showing the fluctuations in heterodyne signal intensities which are caused by speckle noises, by using the optical heterodyne detection method described in FIG. 19.

In FIGS. 20 and 21, laser beams each having a beam diameter of 1 mm and a wavelength of 1.064 $\mu$m are incident onto a 5 mm-thick slab of potato (FIG. 20) and a 5 mm-thick slab of lean pork (FIG. 21), and lights transmitted though the respective samples are detected by a heterodyne detector. FIGS. 20 and 21 have abscissas which represent time in the unit of seconds and minutes, respectively.

As seen from FIGS. 20 and 21, the time periods of heterodyne signal intensity fluctuations can significantly vary with types of scattering samples. It is well known that in the presence of speckle noises the statistics of heterodyne signal intensity follows the Rayleigh distribution with a standard deviation σ=1. Meanwhile, it is also known that speckle noises can be averaged out by averaging the heterodyne detection signals. However, as shown in the example of FIG. 21, when in the sample about two minutes are required for the speckle pattern to change to the next statistically random state, it takes a considerably long period of time to average out the independent speckles by this speckle averaging method.

The reduced heterodyne detection efficiency and speckle noises described are common in heterodyne detection of signal light reflected from the sample as well. Although optical heterodyne detection has been chosen as a typical example, it is understood that other measurement methods based on optical interference may share these problems in common.

SUMMARY OF THE INVENTION

Wherefore, an objective of the present invention is to provide an optical measurement device which improves the heterodyne detection efficiency in the presence of surface scattering, and also average out the speckle noises, so that a highly precise measurement can be realized.

To achieve the above-mentioned objective, the present invention provides an optical measurement device which is equipped with:

(1) a light source for emitting a light beam;

(2) an optical interference system for splitting the light beam emitted from said light source into a signal light passed via a sample position in which a sample is disposed and a reference light passed via an optical path different from the optical path via the sample position, and for superimposing the signal light which has been passed via said sample position onto the reference light which has been passed via the different optical path to produce an optical interference where the signal light and the reference light interfere with each other;

(3) a photo detector array for receiving the superimposed signal and reference lights, obtained by said optical interference system, to obtain a received optical signal.

In said optical interference system (2), light emerging from a concerned point on the path of said signal beam, either on the surface or the inside of a sample disposed in said sample position, is transferred to said photo detector array and superimposed with the reference light.

The said photo detector array (3) has a plurality of spatially arranged detector elements capable of independently detecting the received signal lights; and (4) a signal processing unit for summing said plural optical signals obtained by said photo detector to produce a signal which corresponds to said concerned point.

In the optical measurement device according to the present invention, formed is an image of the concerned point, that is, the present noticed point can be regarded as a single point in respect of a resolution in optical measurement. The photo detector is constituted of multiple detector elements, spatially arranged for independently detecting the arriving signal lights.

As described with reference to FIG. 19, the signal light emerging from the sample 100 is scattered by its optically coarse exit-surface 100a. According to the present invention, for example, a point on the exit surface 100a via which the signal light is emitted from the sample 100 is chosen as the concerned point. On the observation plane, disposed is the photo detector array with multiple detector elements. On the surface of the photo detector array, the signal light is superimposed and thus interfered with the reference light which is constituted of, for example, a plane wave. Because of the surface scattering at the exit surface 100a, the signal light received by the detector array is spatially distorted, that is, its phase distribution is spatially random. Consequently, the phases of the heterodyne detection signal outputs from the detector elements are also random. Although their phases are random, the outputs from the detector elements of a detector array all relate to an identical point on the exit surface, and therefore, can be summed up to reproduce partially or fully the signal light emerging from the exit surface via the concerned point. In the present invention, since the signal lights scattered in broad directions is collected and detected by the photo detector array, the amount of signal light that can be detected is largely increased. Meanwhile, by summing the outputs from the element detectors of a photo detector array, the signal fluctuations caused by speckle noises can be averaged out. As a result, measurement with a considerably improved signal-to-noise ratio, S/N, can be achieved. Specifically, in the conventional heterodyne detection method using a single element detector speckle noises can be averaged out by averaging the detector output as a function of time. Compared to such a temporally averaging method, the present invention offers a spatially averaging method which can remarkably speed up the process of speckle averaging, in addition to providing an increased amount of signal light that can be detected by the heterodyne detection method.

On the other hand, it has been recently demonstrated that by using a photo detector array in heterodyne detection, multiple heterodyne signal outputs can be obtained from the detector array (refer to Electronics Letters, Vol.30, 1753 (1994) K. P. Chan, M. Yamada, H. Inaba). However, what is formed on the surface of the detector array in an image of a concerned region, and information on respective points in the concerned region is obtained by the corresponding detector elements. In other words, instead of scanning the points one by one to successively obtain the information, the information on multiple points which are expanded two-dimensionally is obtained simultaneously. The present invention is intrinsically different from the conventional method in that the information originated from a single point is to be obtained by the spatially arranged, multiple detector elements.

Here, in the optical measurement device based on the present invention, the optical interference system may be provided with a frequency shifter which relatively shifts a frequency of the signal light and a frequency of a reference light. Alternatively, the light source may be a light source emitting a coherent light whose frequency is modulated periodically.

In either of the aforementioned constitutions, the frequencies of the signal light and the reference light can relatively differ from each other.

In order to scan the sample with the signal light in the optical measurement device based on the present invention, the optical interference system preferably includes a scanning mechanism which moves one-dimensionally or two-dimensionally at least one of the sample disposed in the sample position and the signal light in the sample position.

By the provision of the scanning mechanism, a one-dimensional or two-dimensional information distribution of the sample can be obtained.

Also, the optical interference system preferably includes a rotation mechanism which relatively rotates at least one of the sample disposed in the sample position and the signal light in the sample position.

For example, when the present invention is applied to an optical CT (computed tomography) or the like, the rotation mechanism is needed.

Furthermore, in the optical measurement device of the present invention, the optical interference system is preferably provided with an optical image forming system for forming an image of the concerned point on a predetermined focal plane, and an aperture disposed on the focal plane.

By the provision of the constitution described above, in accordance with an opening size of the aperture, the beam diameter of the signal light, i.e., a spatial expansion of the "concerned point" can be freely controlled. Also, unnecessary scattered light components can be reduced. Such an constitution is effective for the enhancement of spatial resolution in an optical measurement.

Furthermore, in the optical measurement device based on the present invention, the signal processing unit may rectify and sum up the multiple heterodyne-detection outputs from the detector elements of a photo detector array.

For example, when obtaining an image constituted of a distribution of a certain measured value for each concerned point of the sample, the signal processing method can be used.

Alternatively, in the optical measurement device of the present invention, the signal processing portion may match phases of the heterodyne signal outputs from the detector elements constituting the photo detector array before summing these signals.

This kind of signal processing method is suitable for obtaining information from the frequency as well as phase of the heterodyne signal, for example, for use in a laser Doppler velocimeter and the like.

BRIEF DESCRIPTION OF THE DRAWINGS

FIG. 13 is a block diagram showing an inner constitution of a signal processing circuit shown in FIG. 12.

FIG. 15 is a schematic diagram of a fifth embodiment of the optical measurement device according to the present invention.

DETAILED DESCRIPTION OF PREFERRED EMBODIMENTS

Embodiments of the present invention will be described with reference to the accompanying drawings.

Figure 1:
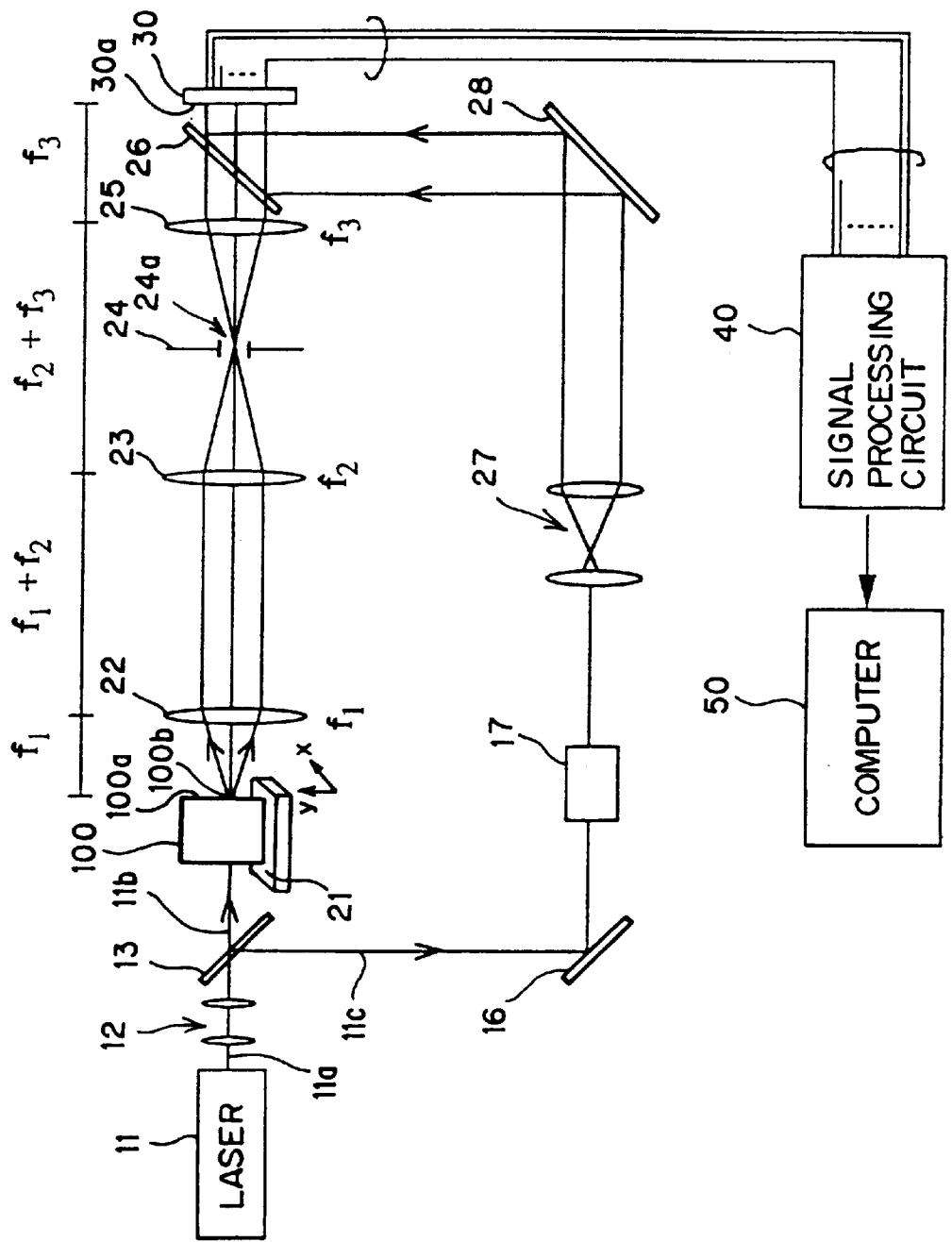
FIG. 1 is a schematic diagram of a first embodiment of an optical measurement device according to the present invention.
Figure 2:
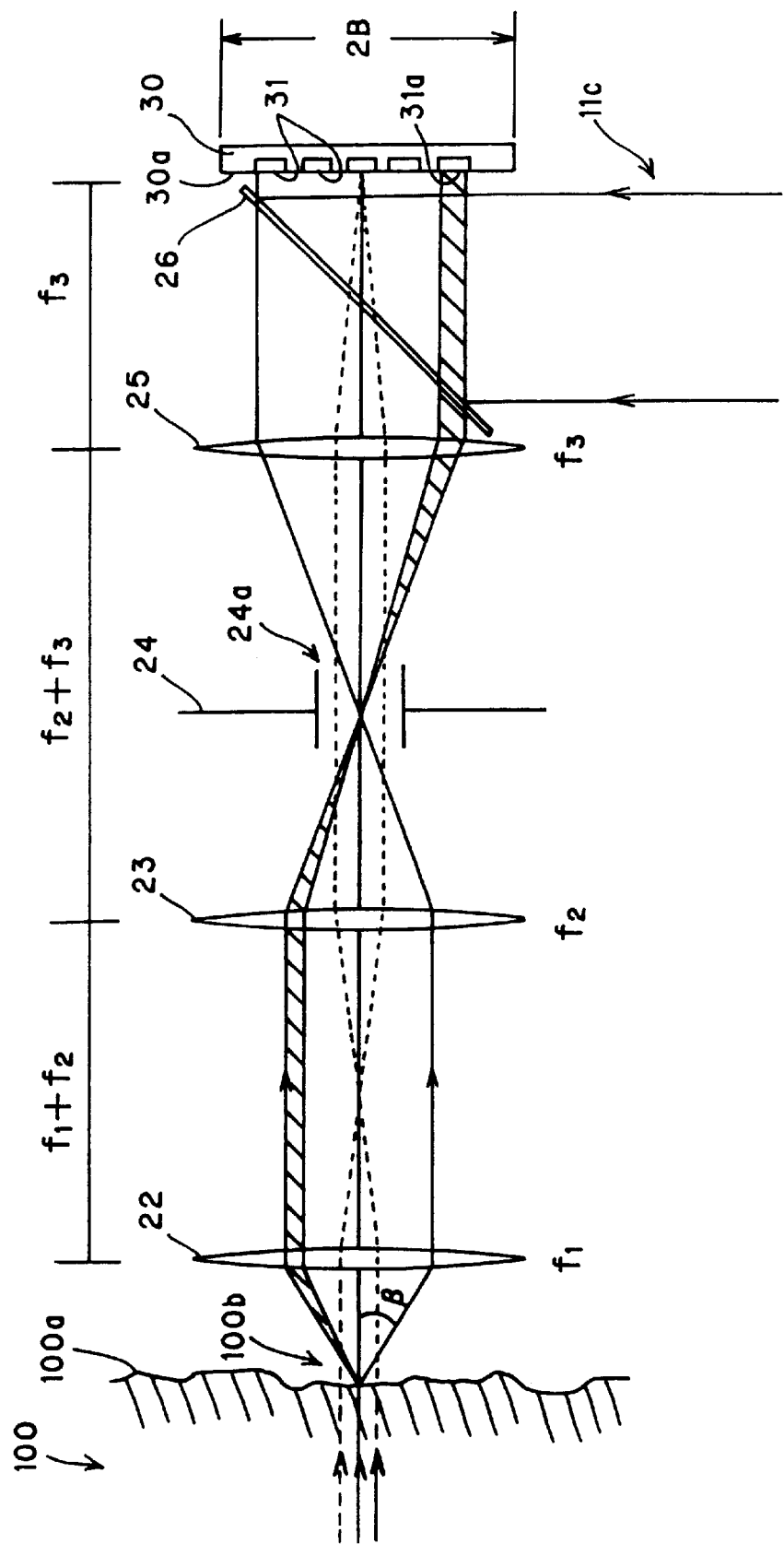
FIG. 2 is a partial enlarged view of the first embodiment shown in FIG. 1.

FIG. 1 is a schematic diagram showing a first embodiment of an optical measurement device according to the present invention, and FIG. 2 is a partial enlarged view of the first embodiment shown in FIG. 1.

A coherent laser beam 11a emitted from a laser source 11 is collimated by lenses 12 to become a light beam having a predetermined beam diameter, and split by a beam splitter 13 into a signal light 11b and a reference light 11c. The signal beam 11b is incident upon a sample 100, which is, for example, a highly scattering medium. The sample 100 is mounted on a scanning stage 21 movable in x- and y-directions. Given that it is not totally distinguished due to scattering inside the sample, a part of the incident signal light may transmit through the sample without being scattered. Meanwhile, there is another component of transmitted signal light, which, despite of being multiply scattered inside the sample, retains partially the coherence of the incident signal light and also emerges from the sample in the vicinity of the optical axis. Intrinsically, the majority of transmitted lights through a highly scattering sample is the diffuse light component.

FIG.1 shows an optical path of the signal light emerging from a concerned point 100b on the optical axis of an exit surface 100a of the sample 100.

The light emerging from the exit surface 100a of the sample 100 is collected by lens 22 which has a focal point on the concerned point 100b and a focal length of $f_1$, and is passed via a lens 23 which has a focal length of $f_2$, to form an image of the exit surface 100a of the sample 100 on a focal plane on which an aperture 24 is disposed.

The signal light passed through an opening 24a in the aperture 24 is passed via a lens 25 which has a focal point on the opening 24a in the aperture 24 and a focal length of $f_3$, further passed through a beam splitter 26, and then incident upon the surface 30a of a photo detector array 30.

On the other hand, the reference light 11c separated from the signal light 11b by the beam splitter 13 is reflected by a mirror 16 and frequency-shifted by a frequency shifter 17. The beam diameter of the reference light is expanded by a beam expander 27 to be equal to or larger than that of the signal light transmitted through the lens 25. Then, the reference light is reflected by a mirror 28 and superimposed on the signal light by use of the beam splitter 26. The collimated signal and reference lights are then incident upon the surface 30a of the photo detector array 30. The frequency shifter 17 may be the AOM, or it may use a phase modulator to periodically modulate the phase of the reference light relative to the signal light.

As shown in FIG. 2, on the surface 30a of the photo detector array 30 spatially arranged are multiple detector elements. Because of the narrow field of view restricted by heterodyne detection, the detector elements views the signal light emerging from the concerned point 100b on the exit surface 100a of the sample 100 through different angles, and together they determine the acceptance angle of the scattered light from the sample. For example, the signal light propagated along an optical path shown by slash lines in FIG. 2 is detected by one of the detector elements 31a which constitute the photo detector array 30. In this manner, the signal lights scattered from the concerned point 100b of the sample 100 in different angles are superimposed on the reference light, and they are independently detected by the detector elements of a photo detector array.

The multiple signal outputs from the detector elements 31 of a photo detector array 30 are transferred to a signal processing circuit 40 shown in FIG. 1, and they are summed up to form a single data point which relates to the concerned point 10b. This data point is transferred to a computer 50 where, as required, data communication, detailed signal and/or image processing, and others are performed.

A content of signal processing in the signal processing circuit 40 will be described later.

In the aforementioned measurement, the scanning stage 21 on which the sample 100 is mounted is moved in the x direction and/or y direction, i.e., the sample 100 is moved relative to the signal light 11b. By repeating the measurement, information regarding plural concerned points arranged one-dimensionally and/or two-dimensionally of the sample 100 can be obtained.

The embodiment shown in FIGS. 1 and 2 has been constituted by considering following two respects:

(1) According to the principle of optical heterodyne detection method as applied to the optical measurement of a scattering sample, lights scattered multiple times inside the sample gradually lose their coherence properties, and thus may not contribute to the heterodyne detection signals (refer to, for example, Physics in Medicine and Biology, Vol.42, 855(1997) by K. P. Chan, B. Devaraji, M. Yamada, H. Inaba). In the proposal of applying heterodyne detection method to the optical imaging of highly scattering media (refer to Electronics Letters, Vol. 26, 700 (1990) by M. Toida, M. Kondo, T. Ichimura, H. Inaba), only the signal light emerging from the sample in the same direction of the incident signal beam is being detected. In contrast, the present embodiment extracts, from the signal lights scattered at the concerned point 100b of the sample 100, those that can be interfered with the reference light. In the sense that the present embodiment detects the coherent signal components emerging from a concerned point 100b of the sample 100 in all directions, the present invention is conceptually different from the conventional heterodyne detection method in optical measurement of scattering media. Meanwhile, in the same manner of the conventional heterodyne detection method, the present invention is also capable of heterodyne detecting the near-axis forward scattered lights that retain partially the coherence properties of the incident signal light, besides the unscattered light.

(2) For those transmitted lights who retain partially the coherence properties of the incident beam and are capable to contribute to the heterodyne detection signals, the major coherence loss due to surface scattering on the surface 100a of the sample 100 is not the temporal coherence but the spatial coherence. Therefore, in order to effectively detect those signals lights suffering from such a spatial coherence loss, it is preferable to use a photo detector array with finite element sizes, so that the spatial coherence loss can be compensated to a certain extent.

The embodiment shown in FIGS. 1 and 2 has been constituted based on the aforementioned conception. As it will be described later, remarkable improvements have been confirmed in signal intensity and S/N ratio, as compared to the conventional optical heterodyne detection method. In the following, an optical system for guiding the signal light emerging from the sample 100 to the photo detector array 30 shown in FIG. 2 is described in detail.

If the exit surface 100a of the sample 100 is optically flat, there will be no surface scattering, so that the unscattered component of the transmitted light will emerge from the sample in a manner shown by the dotted lines in FIG. 2. This signal beam is transferred to lens 25 by lense 22 and 23, and then focused onto the center of the photo detector array 30 by the use of lens 25. Since on the surface of the photo detector array 30 the focused signal beam becomes a plane wave, it effectively interfers with the reference light which is also a plane wave. Optical heterodyne detection is thus performed.

If the exit surface 100a of the sample 100 is not optically flat, the transmitted signal light will spread out rapidly due to surface scattering. The present embodiment employs a lens 22 to collect such a scattered light. The distance between the concerned point 100b and the lens 22 is maintained to be about equal to the focal length of lens 22, so that after transmitting through lens 22 the collected signal light from the concerned point 100b becomes collimated. This collimated signal beam is further transferred to the photo detector array 30 via lenses 23 and 25, and interfers with the reference light. Optical heterodyne detection is thus performed.

In the present embodiment, between the lens 23 and the lens 25 disposed is an aperture 24. By reducing the diameter of the opening 24a in the aperture 24, in the similar manner as a conventional confocal microscope (refer to, for example, "Confocal Microscopy" edited by T. Wilson and published by Academic Press (London, 1990)), a high spatial resolution can be obtained irrespective of the diameter of the laser beam incident on the sample 100. However, as compared to the conventional confocal optical microscope using direct detection method, the present embodiment employs optical heterodyne detection method, and, further inventively, a photo detector array for the heterodyne detection of spatially distorted signal lights, instead of using a single detector.

For the purpose of decreasing the amount of unnecessary scattered lights reaching the photo detector array 30, the diameter of the opening 24a in the aperture 24 does not necessarily have to be reduced. The aperture diameter may be adjusted freely. This respect is also one of the advantages offered by the provision of aperture 24. If the amount of scattered lights reaching the detector array 30 is large, not only the components which simply fail to contribute to heterodyne detection but the shot noises in optical heterodyne detection will be increased. Therefore, the unnecessary scattered lights are preferably prevented from reaching the photo detector array 30. The aperture 24 is suitable for this purpose.

By appropriately choosing the focal length $f_2$ and $f_3$ of the lenses 23 and 25, respectively, the beam diameter of the signal light beam can be enlarged or reduced in accordance with the size of the photo detector array 30. According to geometric optics, the diameter of the signal beam incident onto the photo detector array 30, $d_2$, is given as follows, $$d_2 = M \times d_1 \tag{1}$$

where $d_1$ is the diameter of the signal beam transmitted through lens 22, and $M = f_3/f_2$ is the optical magnification.

On the other hand, by its optical interference nature heterodyne detection has a considerably narrow field of view $\Theta$, given by $\Theta \equiv \lambda/D$, where $\lambda$ is the wavelength of the signal light, and D is the diameter of a photo detector. Because of this narrow field of view, the detector elements 31 of the photo detector array 30 view the signal light emerging from the concerned point 100b of the sample 100 through different angles, and together they determine the acceptance angle, $2\beta$, of the scattered light from the sample. According to geometric optics, when the size of the total detection area of a photo detector array 30 is given as 2B, it is calculated that $$\tan\beta = (B/f_1) \times (f_1/f_3) \tag{2}$$
$$= (B/f_1) \times (1/M)$$

In conventional optical heterodyne detection, only the signal light arriving the detector within its narrow field of view can be effectively detected. In contrast, the present embodiment combines the field of views of the individual detector elements 31 of a photo detector array 31 to form an acceptance angle for the signal light scattered at the concerned point 100b of the sample 100. That in principle this acceptance angle can be widened by appropriately choosing the array size 2B also makes the present invention outstanding from the conventional heterodyne detection using a single element detector.

Figure 3:
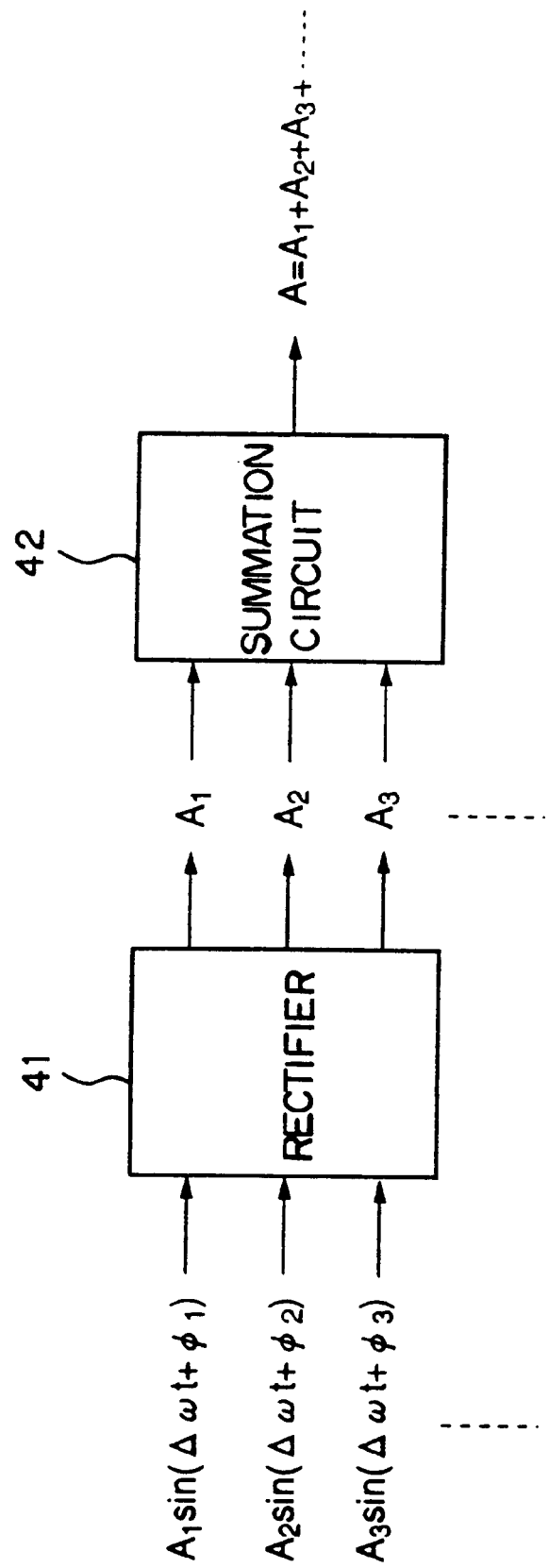
FIG. 3 is a block diagram showing an inner constitution of a signal processing circuit shown in FIG. 1.
Figure 4A:
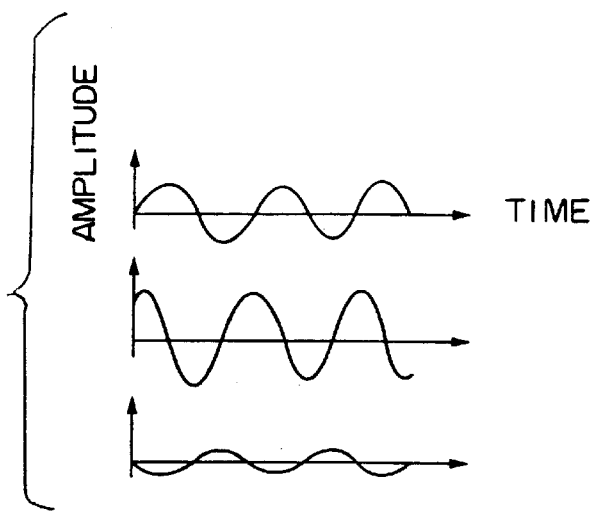
FIGS. 4A to 4C are explanatory views of a signal processing method in the signal processing circuit shown in FIG. 1.
Figure 4B:
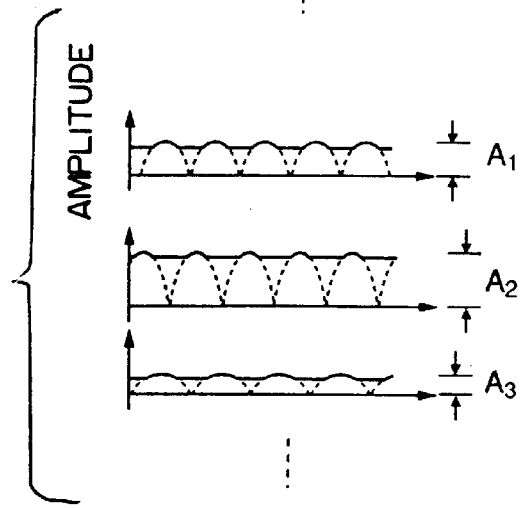
Figure 4C:
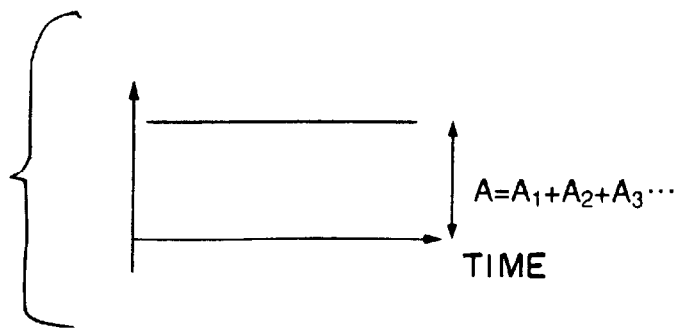

FIG. 3 is a block diagram which diagrammatically shows the constitution of the signal processing circuit 40 shown in FIG. 1, and FIG. 4 is an explanatory view of the signal processing carried out inside.

The ways of signal processing for signal outputs from a photo detector array 30 can be classified into the incoherent summation method and the coherent summation method. The following is a description of the incoherent summation method.

The heterodyne signal outputs from the detector elements 31 constituting the photo detector array 30 can be given in the forms $A_1 \sin(\Delta\omega t + \phi_1)$ $A_2 \sin(\Delta\omega t + \phi_2)$ $A_3 \sin(\Delta\omega t + \phi_3)$ Where $\Delta\omega = 2\pi\Delta f$ denotes a difference in angular frequencies between the signal light and the reference light; $A_1$, $A_2$, $A_3$, ... are the amplitudes of heterodyne signals; and $\phi_1$, $\phi_2$, $\phi_3$, ... are the phases of heterodyne signals. Generally, the amplitudes $A_1$, $A_2$, $A_3$, ... and the phases $\phi_1$, $\phi_2$, $\phi_3$, ..., as shown in FIG. 4A, differ from one another.

The signal processing circuit 40 shown in FIG. 1 is, as shown in FIG. 3, provided with a rectifier 41 and a summation circuit 42. Plural heterodyne signals $A_1 \sin(\Delta\omega_r + \phi_1)$, $A_2 \sin(\Delta\omega_r + \phi_2)$, $A_3 \sin(\Delta\omega_r + \phi_3)$, ... which from the detector elements 31 of the photo detector array 30 are transferred to the rectifier 41, and, as shown in FIG. 4B, they are rectified and converted to the direct-current (DC) signals with amplitudes proportional to the amplitudes of the heterodyne signals.

The DC signals are then input to the summation circuit 42 and summed up to form a DC signal $A = A_1 + A_2 + A_3 + \cdots$. As such, the DC signal A is carrying the information regarding the concerned point 100b shown in FIGS. 1 and 2.

By successively performing the signal processing while scanning stage 21 shown in FIG. 1, for example, in both x and y directions, a two-dimensional image data of the sample 100 can be obtained.

An optical system and a signal processing unit based on the embodiment shown in FIGS. 1–4 have been constructed and applied to demonstrate the feasibility of the embodiment. A description of the results is given as follows.

(Demonstration 1)

Figure 5:
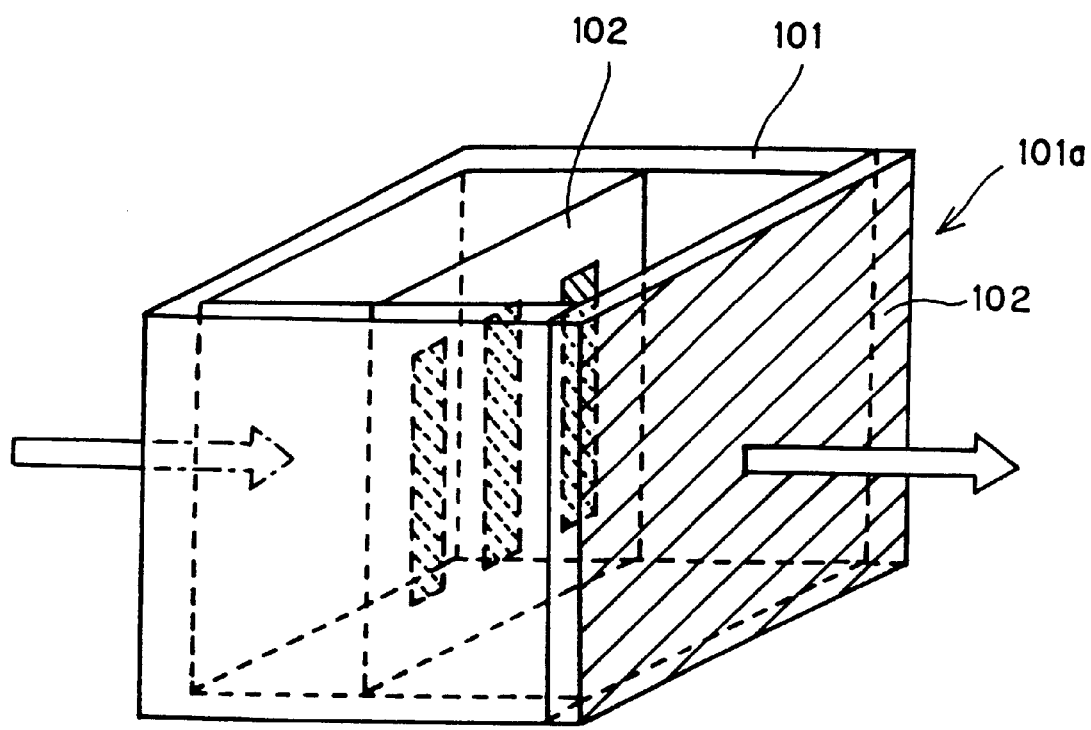
FIG. 5 is a schematic diagram of an artificial sample.

FIG. 5 is a schematic diagram of an artificial sample used in the experiment.

In the experiment, as a sample of scattering body used was a container 101 which contains Intralipid Solution. The thickness of the Intralipid solution as measured in the direction of light transmission is 4 cm. Further, on an exit surface 101a of the container 101 placed was a ground glass 103 for scattering lights to simulate light scattering on the exit surface of the sample. Further, into the container 101 inserted was a chart 102 which has three opaque bars each having a width of 1 mm. The attenuation for the unscattered light through the scattering sample shown in FIG. 5 is −70 dB, that is, the transmitted, unscattered light is attenuated to $10^{-7}$ of the incident light.

Figure 6A:
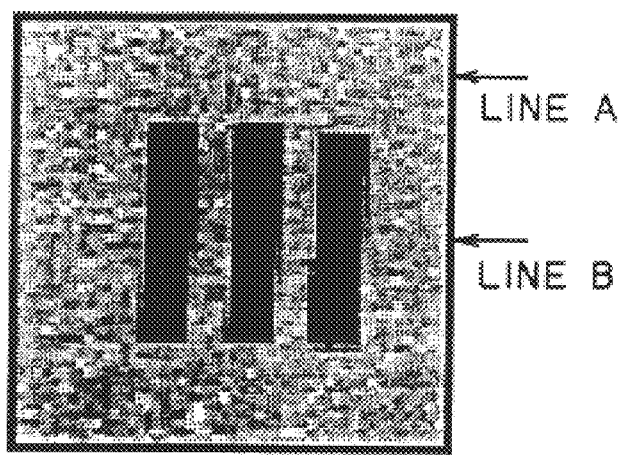
FIGS. 6A to 6C show measurement results of the artificial sample shown in FIG. 5 according to the embodiment.
Figure 6B:
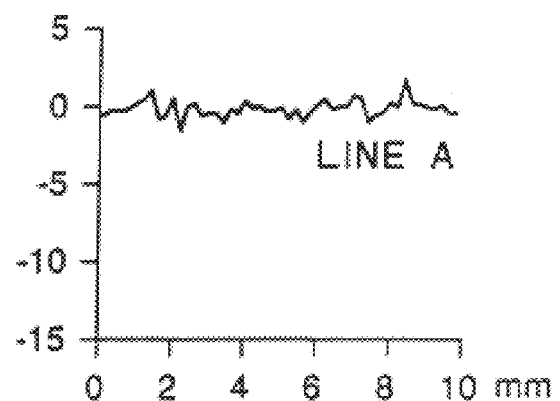
Figure 6C:
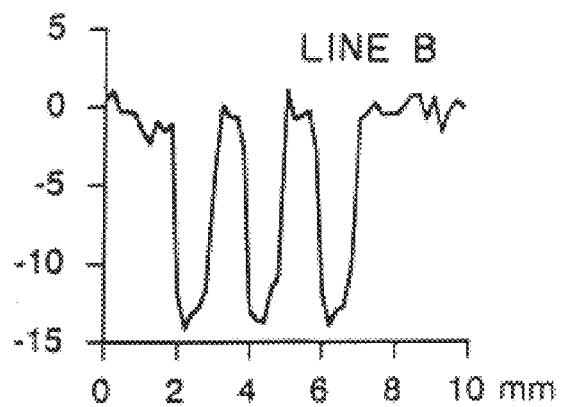
Figure 7A:
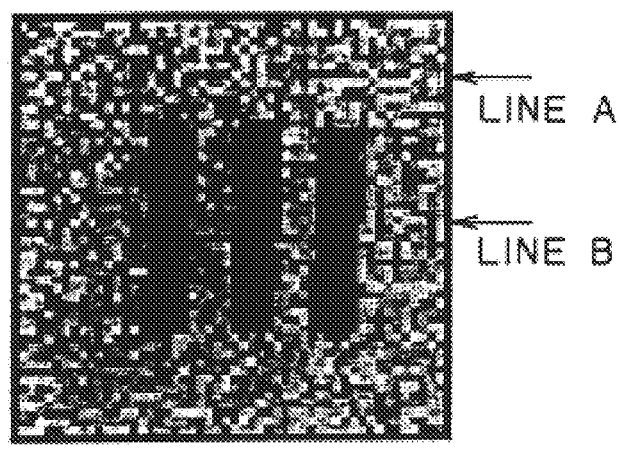
FIGS. 7A to 7C show measurement results of the artificial sample shown in FIG. 5 according to a conventional optical heterodyne method (refer to FIG. 17).
Figure 7B:
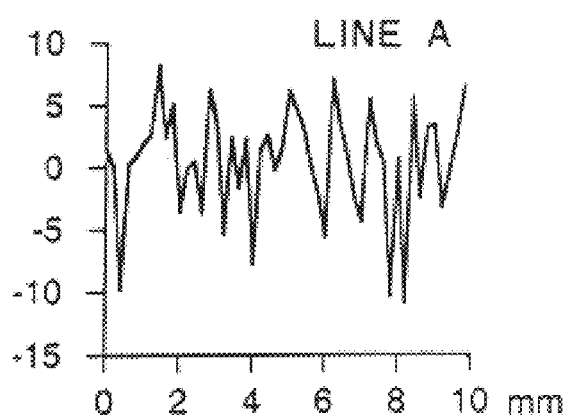
Figure 7C:
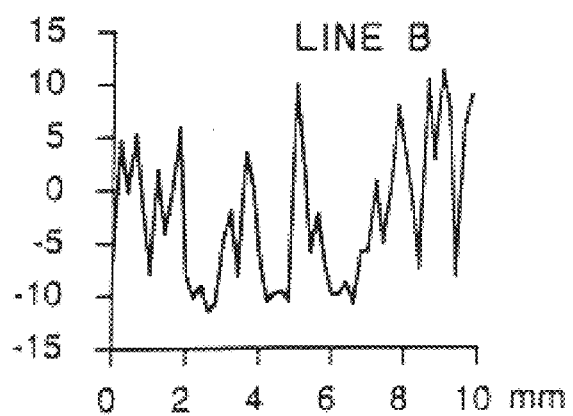
Figure 18:
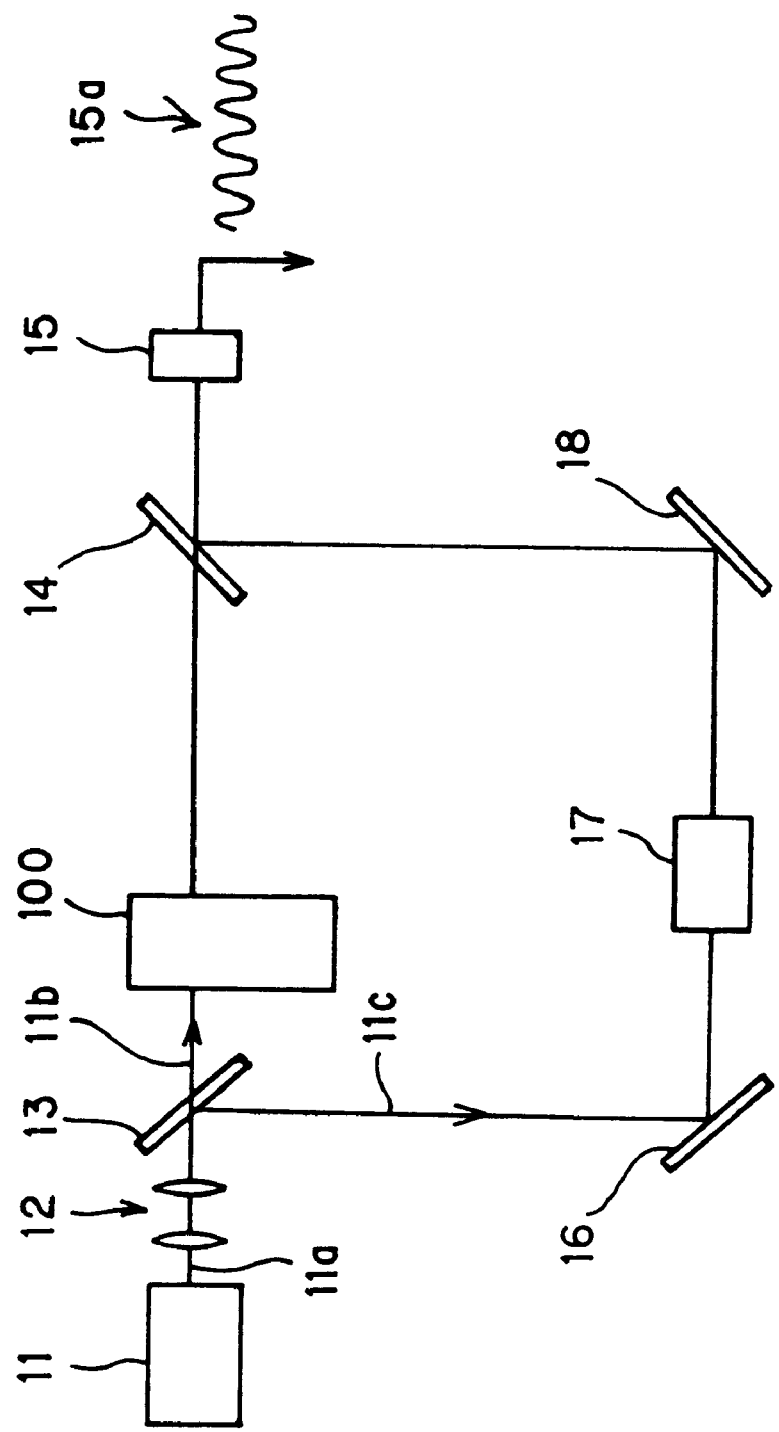
FIG. 18 is a principle diagram of an optical heterodyne detection method.
Figure 19:
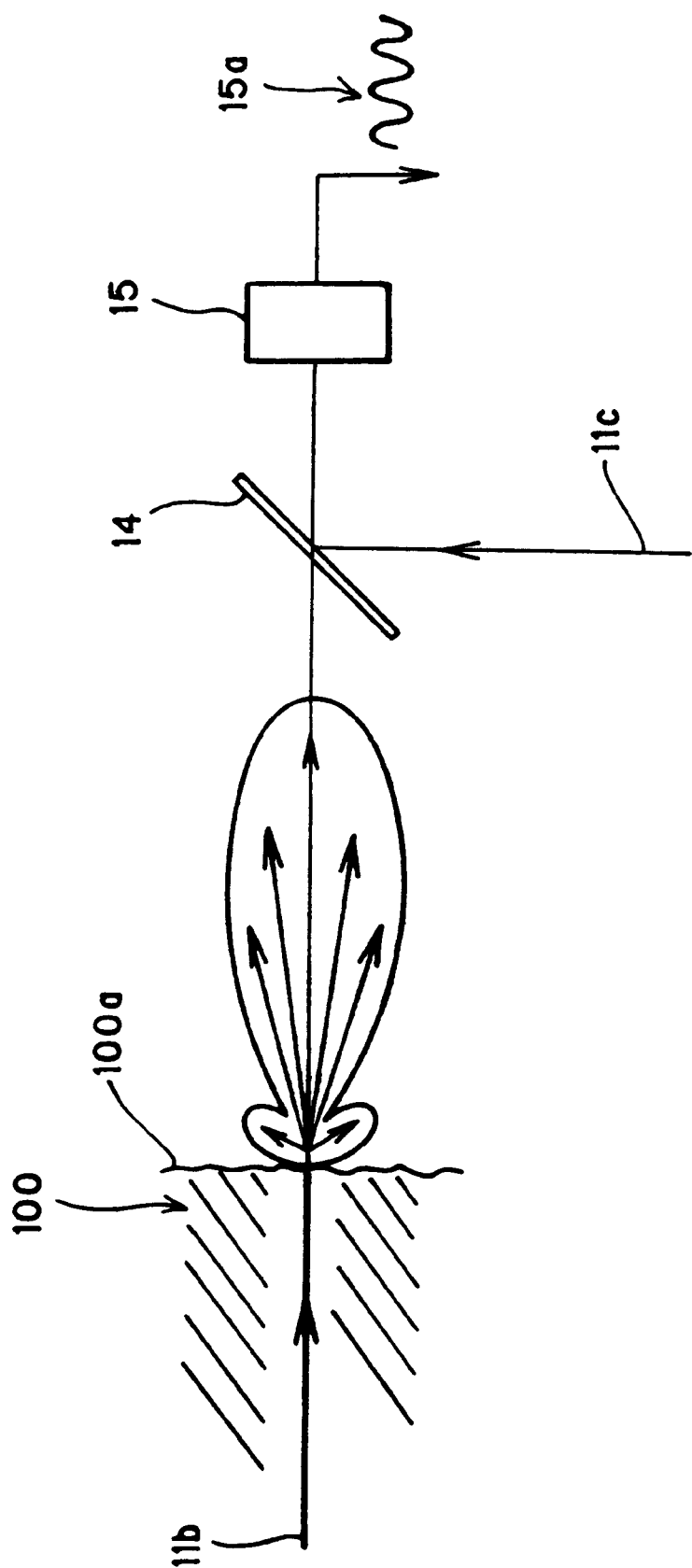
FIG. 19 is an explanatory view of a practical issue associated with the optical heterodyne detection method.
Figure 20:
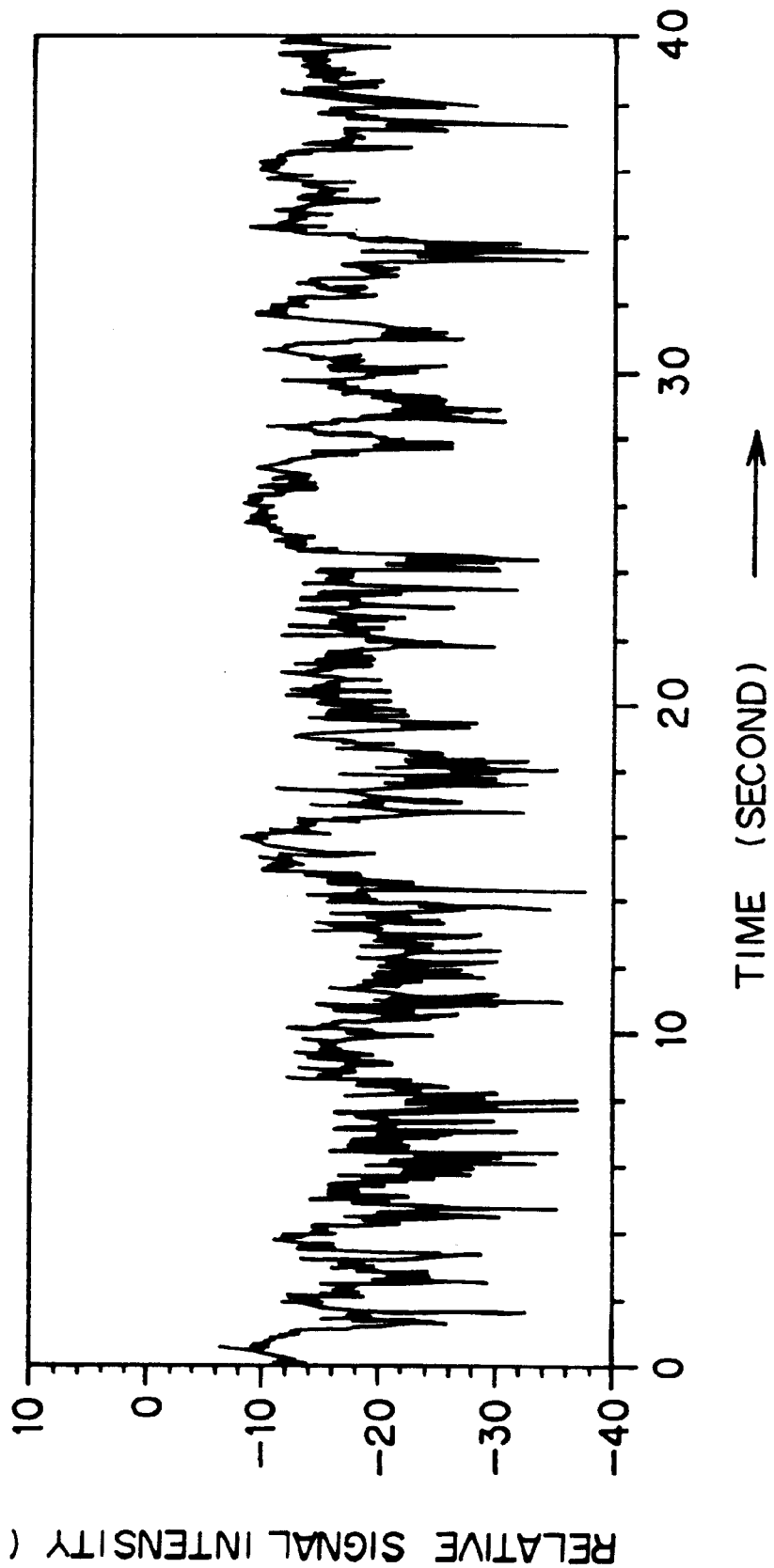
FIG. 20 is a graph showing a measurement example of fluctuations in heterodyne signal intensities, caused by speckle noises when the optical heterodyne detection method is used.
Figure 21:
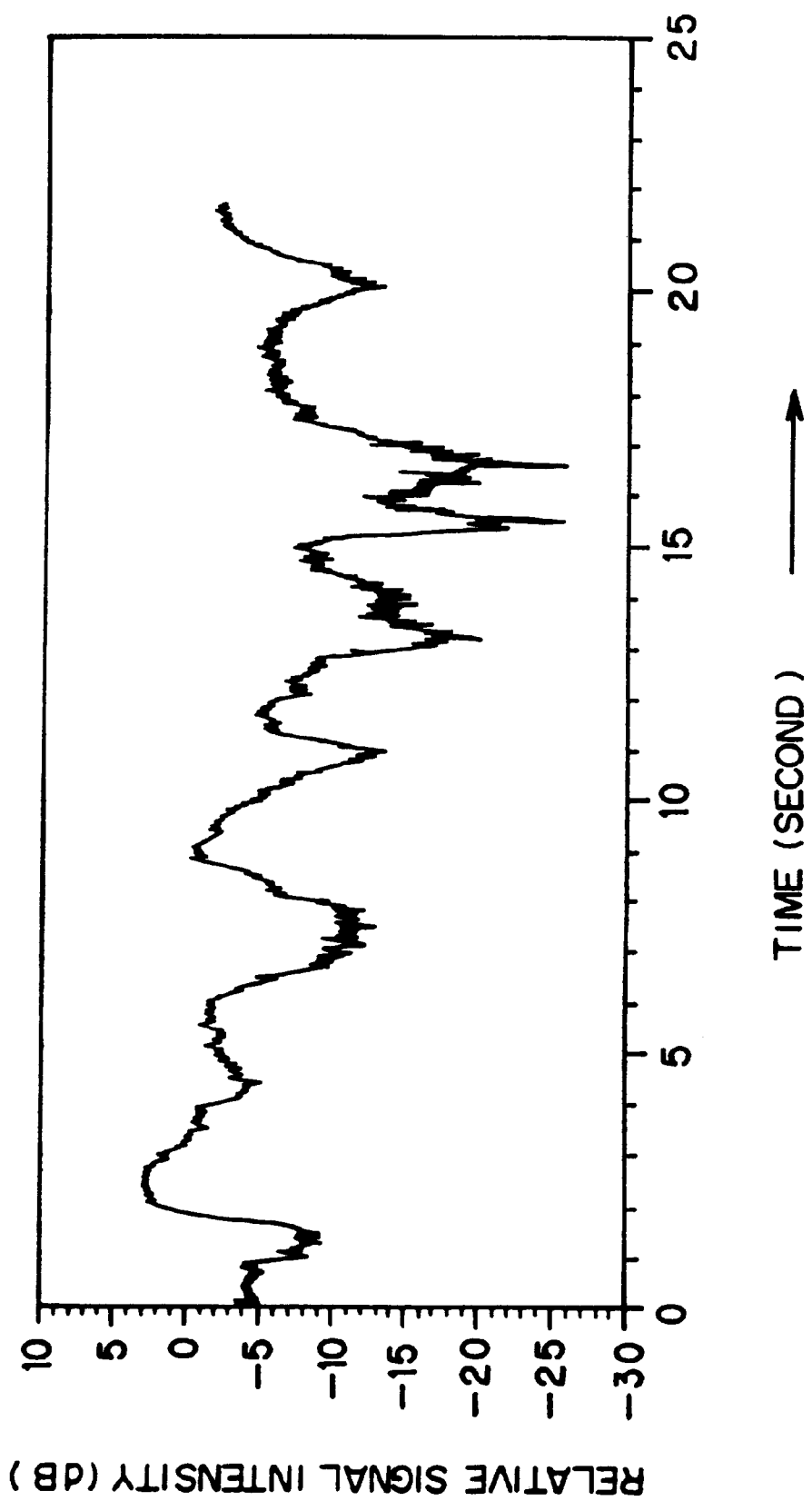
FIG. 21 is a graph showing another measurement example of fluctuations in heterodyne signal intensities, caused by speckle noises when the optical heterodyne detection method is used.

The measurement results of the artificial sample shown in FIG. 5 by using an optical system and a signal processing system based on the embodiment shown in FIGS. 1 to 4 are shown in FIGS. 6(*a*) to (*c*). For reference, FIGS. 7(*a*) to (*c*) show the measurement results of the artificial sample shown in FIG. 5 by using conventional heterodyne detection method(refer to FIG. 18). FIGS. 6A and 7A each shows a two-dimensional image which is obtained by performing the measurement while moving the artificial sample two-dimensionally. FIGS. 6B and 7B each shows changes in signal level on one line shown as line A in FIG. 6A or 7A. FIGS. 6C and 7C each shows changes in signal level on one line shown as line B in FIG. 6A or 7A. In FIGS. 6B, 6C, 7B and 7C, each axis of abscissa represents the position of the sample on the line A or B, while each axis of ordinate represents a relative value of the signal level in dB. As a laser light source used was Nd:YAG laser with a wavelength of 1064 nm. Also, in the embodiment shown in FIGS. 6A to 6C, as the photo detector array used has detector elements arranged in eight rows and eight columns, totaling 8×8=64.

As instantly apparent from FIGS. 6 and 7, in the present embodiment (FIG. 6), speckle noises are significantly averaged out so that S/N is remarkably improved, as compared with the conventional optical heterodyne detection method (FIG. 7).

(Demonstration 2)

Figure 8:
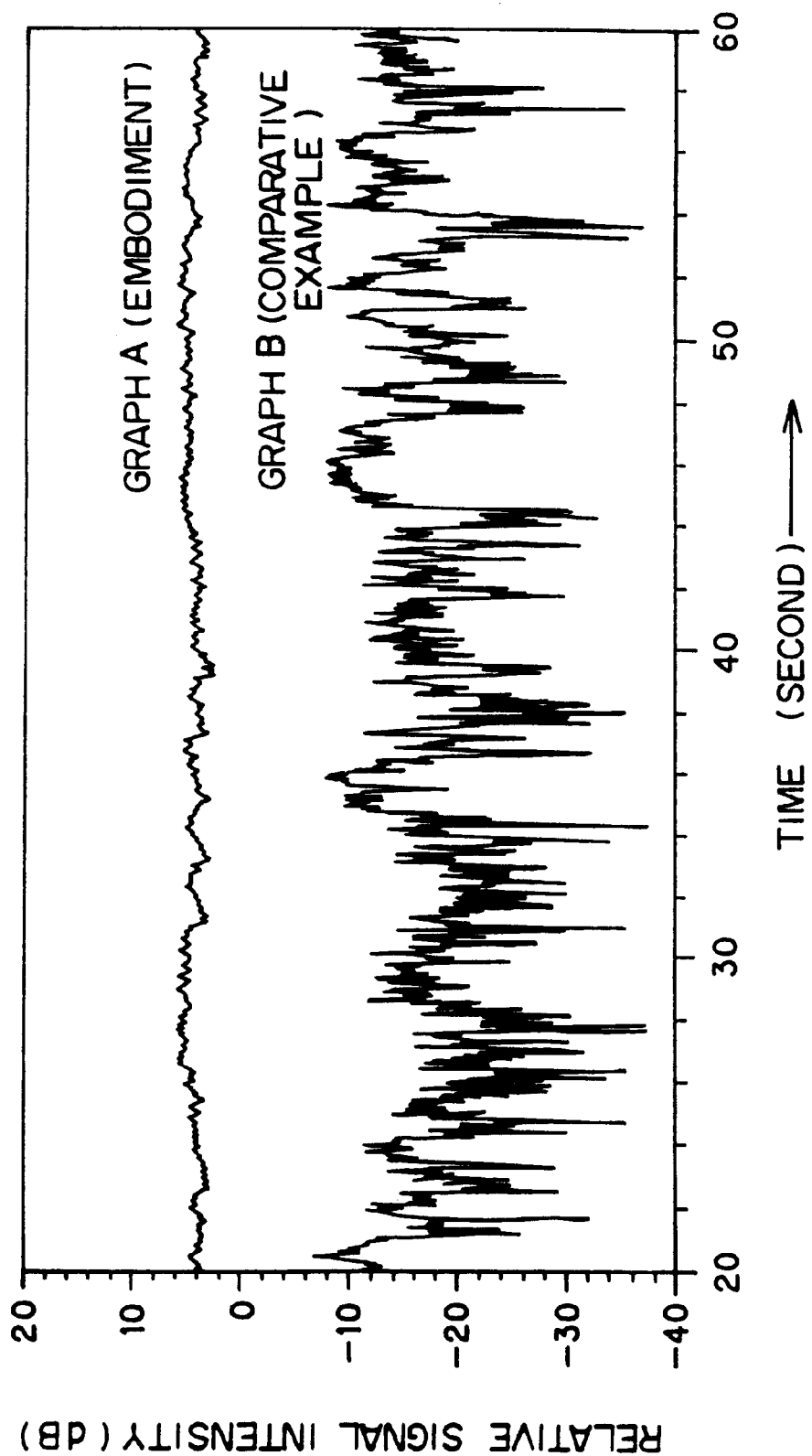
FIG. 8 is a graph showing a measurement result of fluctuations in heterodyne signal intensities, caused by speckle noises.

FIG. 8 is a graph showing a measurement result of fluctuations in heterodyne signal intensities, caused by speckle noises.

In FIG. 8, Graph B depicts changes with an elapse of time in intensity of heterodyne signals when a slab of potato with a thickness 5 mm was measured in the conventional optical heterodyne detection method, while Graph A depicts the changes when the same sample was measured according to the embodiment (obtained by the 8×8=64 detector elements). When these Graphs A and B are compared, in Graph A, the signal intensity is increased by about 60 times, which is proportional to the number of the detector elements (64 elements). This verifies that the coherent components possessed by the transmitted lights emerging from the sample with a wide angle can be heterodyne detected as well.

The transmitted signal light which spreads out rapidly due to surface scattering is, as aforementioned, subject to the spatial coherence loss. Such a scattered light with considerable spatial coherence loss cannot be effectively detected by the photo detector which is constituted of a single detector element (refer to, for example, Optics Letters, Vol. 17, 1237 (1992) by K. P. Chan, D. K. Killinger). Therefore, the present method can be regarded as a highly efficient optical heterodyne detection method.

As seen from FIG. 8 and clearly seen also from the comparison of FIGS. 6 and 7, another characteristic of the embodiment is that speckle noises are largely eliminated. To support this, statistical data is shown as follows.

Figure 9A:
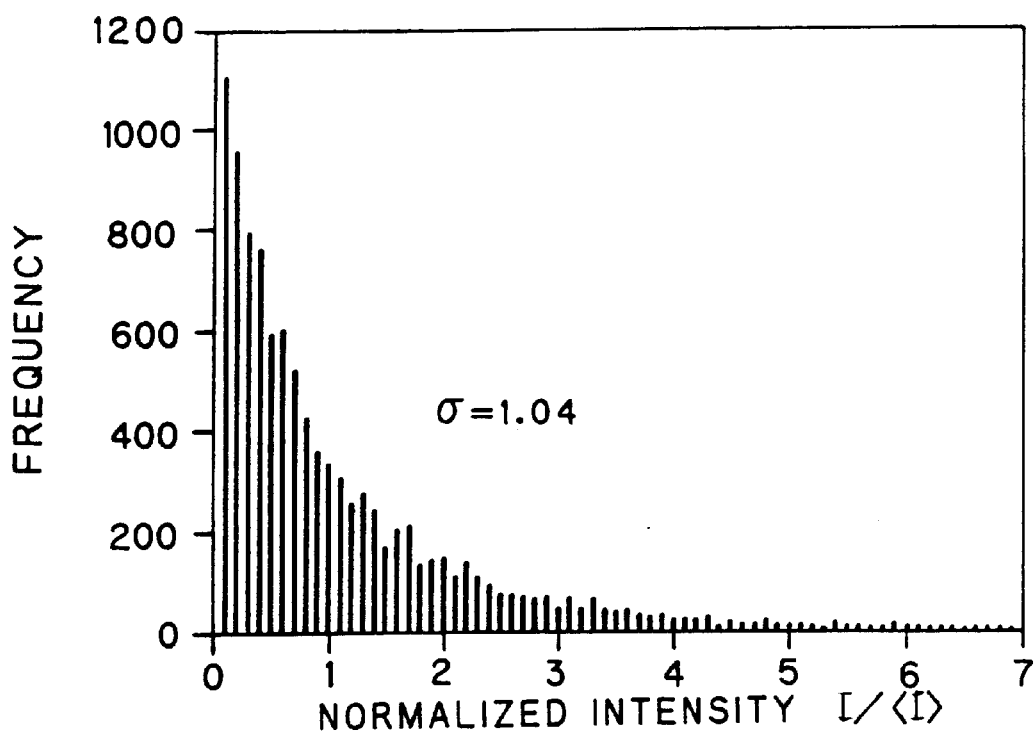
FIGS. 9A and 9B are histograms where the heterodyne signal intensities of lights transmitted through a slab of potato are sampled ten thousand times at a time interval of 20 msec, according to a comparative example and the embodiment, respectively.
Figure 9B:
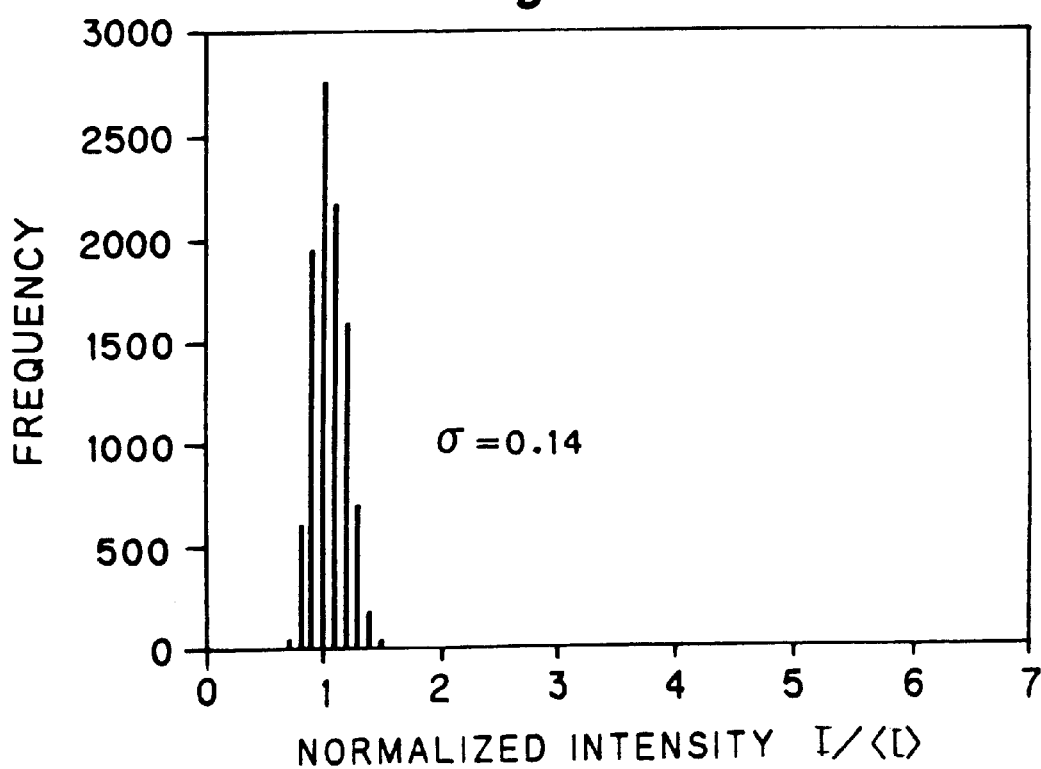

FIGS. 9A and 9B are histograms where heterodyne signal intensities of lights transmitted through slabs of potato are sampled ten thousand times in the conventional optical heterodyne detection method (comparative example) and the detection method according to the embodiment shown in FIGS. 1 to 4 (the lights were detected by the 8×8=64 detector elements), respectively. The heterodyne signal was sampled at a time interval of 20 msec as one data. A standard deviation of ten thousand data points measured in this manner is $\sigma=1.04$ for the conventional method shown in FIG. 9A, which is about equal to that of the speckle noises characterized by the Rayleigh distribution of $\sigma=1.0$. On the other hand, the standard deviation according to the embodiment shown in FIG. 9B is $\sigma=0.14$, and the signal intensity distribution is Gaussian. The smoothing of the signal fluctuations by averaging out the speckle noises is represented by $\sigma=(1/\sqrt{N})$, in which N denotes the times of averaging out the independent speckles. In FIG. 9B, $\sigma=0.14$ is remarkably close to $\sigma=(1/\sqrt{64})=0.125$ as it is chosen that N equals to the number of detector elements, N=64. Therefore, it can be concluded that the present invention enables speckle averaging to be carried out spatially, instead of the temporally averaged method in conventional heterodyne detection.

Figure 10:
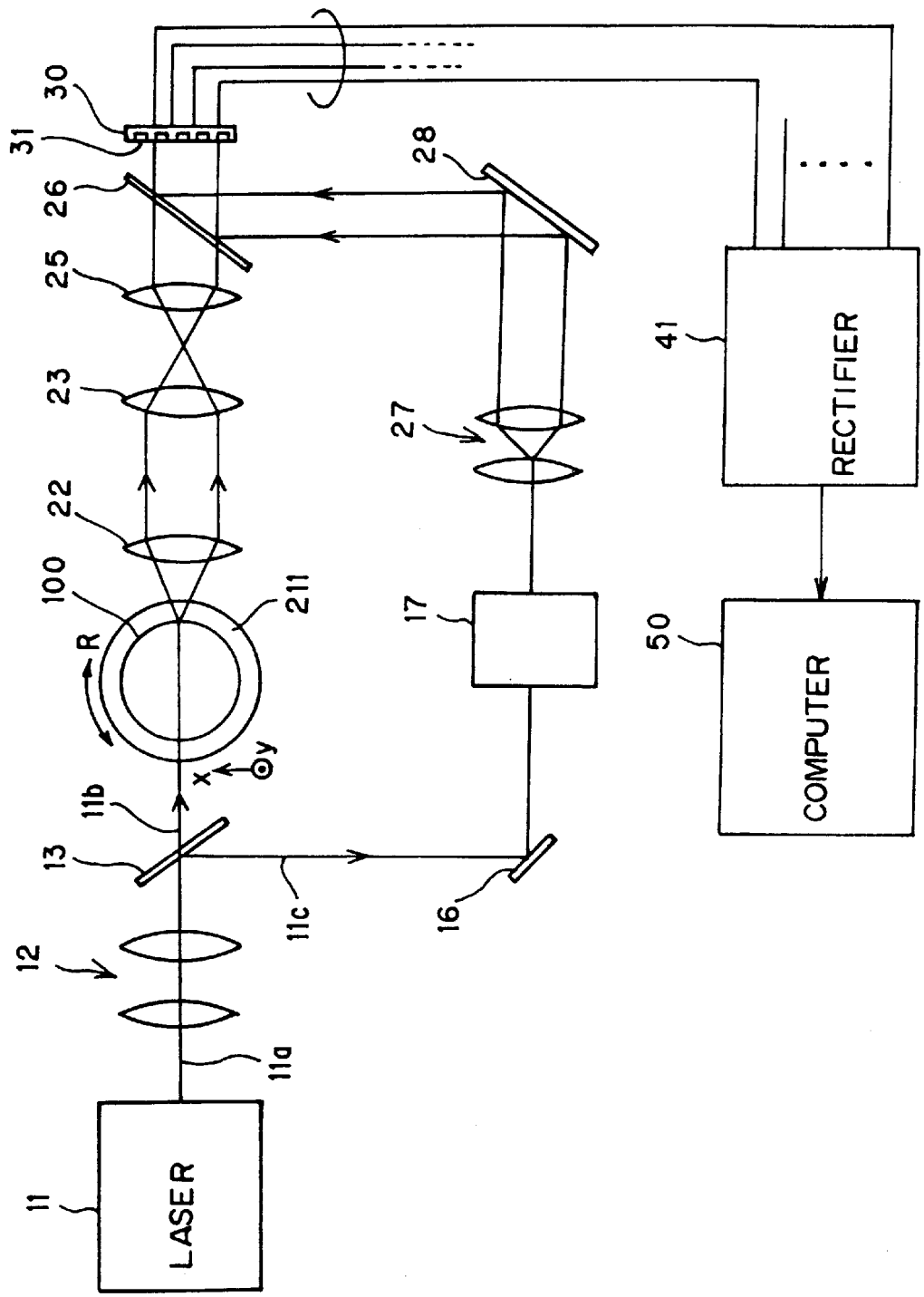
FIG. 10 is a schematic diagram of a second embodiment of the optical measurement device according to the present invention.

FIG. 10 is a schematic diagram of a second embodiment of the optical measurement device according to the present invention. Elements common with those described in the first embodiment are given the same reference numerals as those shown in the figures of the first embodiment. Different respects will be described.

The second embodiment shown in FIG. 10 is different from the first embodiment shown in FIG. 1 in that the scanning stage 21 of the first embodiment shown in FIG. 1 is replaced with a sample mounting stage 211 which can move in both x and y directions while rotating in an R direction, and in that instead of the signal processing circuit 40, shown in FIG. 1, and provided with the rectifier 41 and the summation circuit 42 shown in FIG. 3, only the rectifier 41 is provided, where the heterodyne signals are rectified and transferred to the computer 50 without being summed up.

In the second embodiment, since the sample mounting stage 211 moves in both x and y directions and rotates in the R direction, a three-dimensional CT(computed tomography) image can be constructed from the two-dimensional transmission images measured from various angles, and by using a CT algorithm. Besides the capability of speckle averaging, the wide acceptance angle provide by present prevention enables heterodyne detection to be performed for the signal light emerging from an irregular surface of a scattering sample. This added capability is particularly useful for the precision measurements such as CT.

The replacement of the signal processing circuit 40 shown in FIG. 1 with a rectifier 41 in FIG. 10 means that part of the signal processing may be performed by a computer 50. In FIG. 10, rectification is performed outside the computer 50, while the arithmetic function originally operated by the summation circuit 42 shown in FIG. 3 is performed inside the computer 50. Inside the computer 50, an arithmetic operation for constructing the CT image based on the CT algorithm is also performed.

Figure 11:
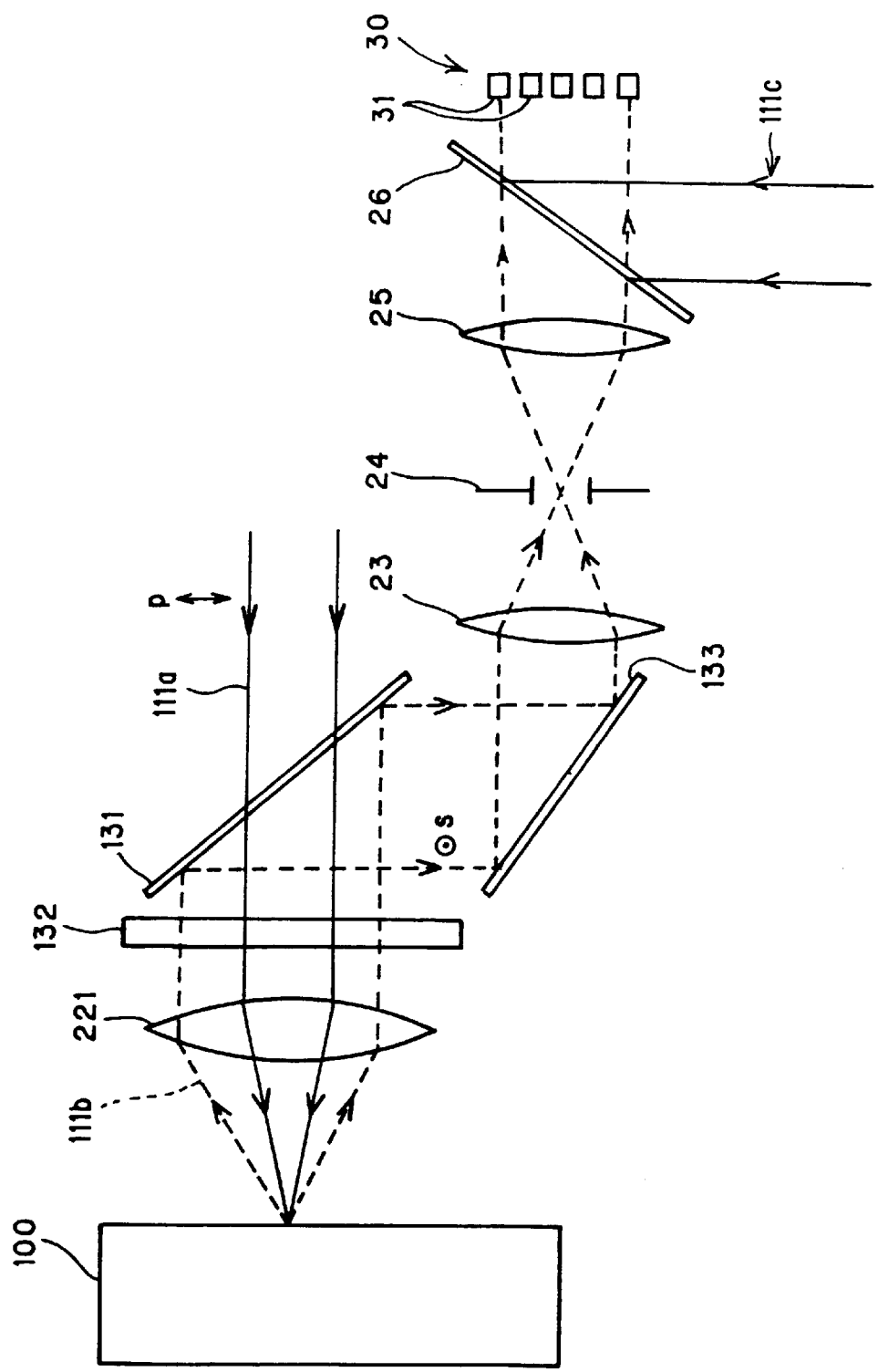
FIG. 11 is a partial view diagrammatically showing an optical system of the optical measurement device according to a third embodiment of the present invention.

FIG. 11 is a partial view diagrammatically showing an optical system of the optical measurement device according to a third embodiment of the present invention. The third embodiment is an example in which the present invention is applied for measuring lights reflected from a scattering body.

A horizontally polarized (P-polarized) laser beam 111*a* is passed as an incident light beam through a polarizing beam splitter 131 and a quarter-wave plate 132 to become circularly polarized, before it is focused onto the surface or at a predetermined depth underneath the surface of the sample 100, by using a lens 221. Although the reflected light from the sample may spread out within an solid angle which is, for example, larger than that of the focusing incident laser beam, a large part of it may be collected by lens 221, and the transmitted light through lens 221 is about collimated. As the collimated signal light passes through the quarter-wave plate 132, it becomes vertically polarized (S-polarized) and it is to be reflected by the polarizing beam splitter 131. The signal light reflected by the beam splitter 131 is further reflected by a mirror 133. Subsequently, in the same manner as the first embodiment shown in FIG. 1, the signal light is transmitted via the two lenses 23 and 25 to the photo detector array 30 in which the multiple detector elements 31 are spatially arranged. Also, the signal lights are superimposed on the reference lights 111*c* by the beam splitter 26, and detected with the optical heterodyne method.

It should be noted that although a coherent light source such as a laser has been chosen in the example of FIG. 11, a light source with low temporal coherence such as a laser wide spectral width, a super luminescent diode, and even a white light source can be employed as well. In this case, by varying the path length difference between the signal light and the reference light, a tomographic image can be obtained by using the reflected lights.

Figure 12:
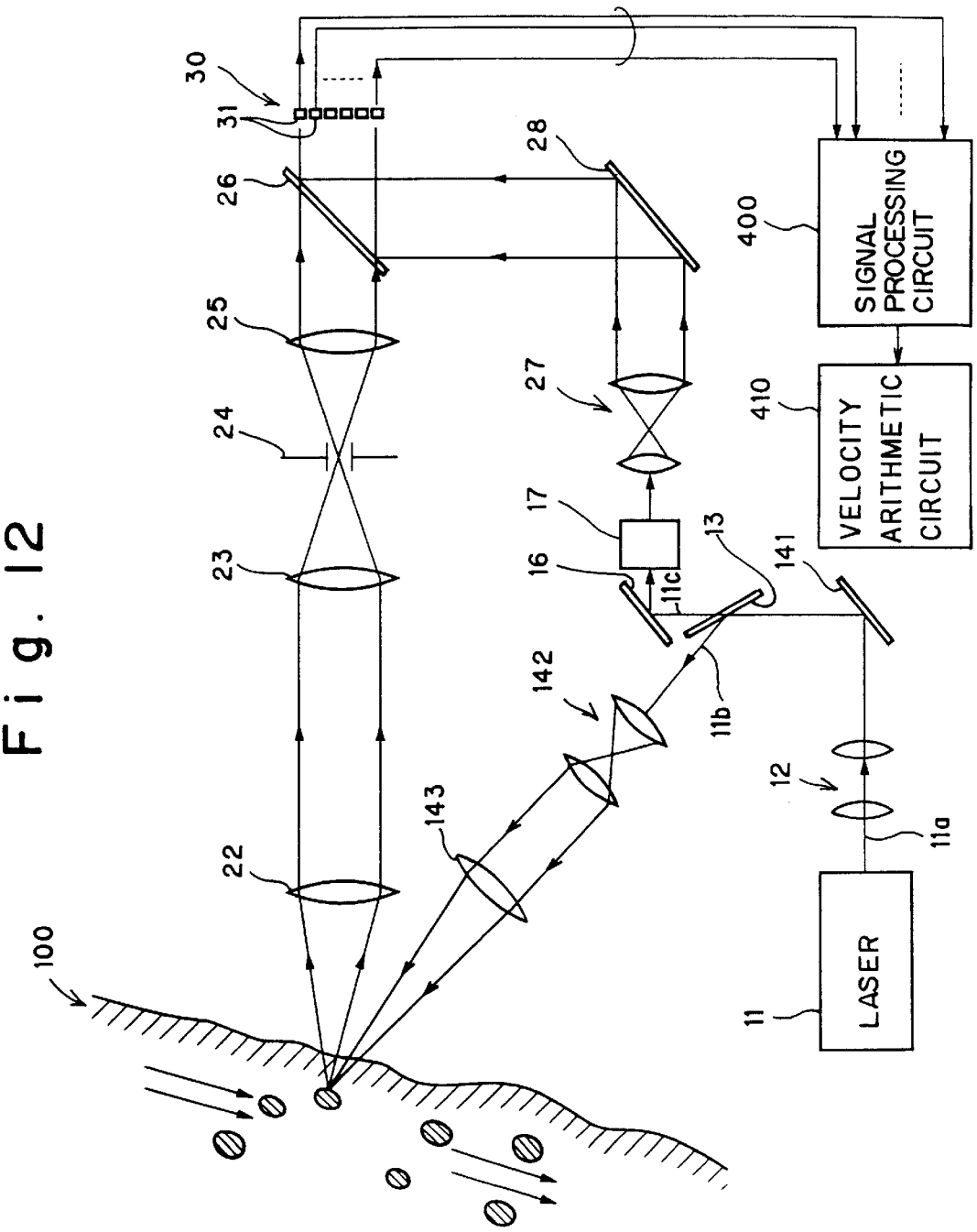
FIG. 12 is a schematic diagram showing a fourth embodiment of the optical measurement device according to the present invention.

FIG. 12 is a schematic diagram showing a fourth embodiment of the optical measurement device according to the present invention. Here, an example in which the present invention is applied to the laser Doppler velocimeter is shown.

A velocimeter based on the measurement of the Doppler shift of a laser beam is generally called the laser Doppler velocimeter. Here, a laser velocimeter which is constituted to measure the speed of a fluid is referred to as the laser Doppler velocimeter. The laser Doppler velocimeter measures the amount of Doppler shift for lights reflected by the fluid itself or by the scattering body flowing in the fluid.

As the reflected light may suffer from a spatial coherence loss due to scatterings on the sample surface and/or inside the fluid, there exists a merit of applying the present invention to laser Doppler velocimeter.

The laser light beam 11a emitted from the laser light source 11 is collimated by the collimator lenses 12, reflected by a mirror 141, and split into the signal light 11b and the reference light 11c by the beam splitter 13. The reference light 11c is passed via the same optical arrangement as that in the first embodiment shown in FIG. 1, before incident onto the photo detector array 30.

The signal light 11b separated from the reference light 11c by the beam splitter 13 has its beam diameter expanded by a beam expander 142, and is focused into the sample (fluid) 100 by an objective lens 143. The signal lights reflected by the sample (fluid) 100 itself or the scattering body in the sample (fluid) are collected by lens 22. Subsequently, in the same manner as the first embodiment shown in FIG. 1, the signal lights are incident onto the photo detector array 30.

The heterodyne signal outputs from the multiple detector elements 31 constituting the photo detector array 30 are transferred to a signal processing circuit 400. In the signal processing circuit 400, an arithmetic operation is performed with a coherent summation method.

FIG. 13 is a block diagram showing an inner constitution of the signal processing circuit 400 shown in FIG. 12, and FIG. 14 is an explanatory view of its signal processing method.

Figure 14A:
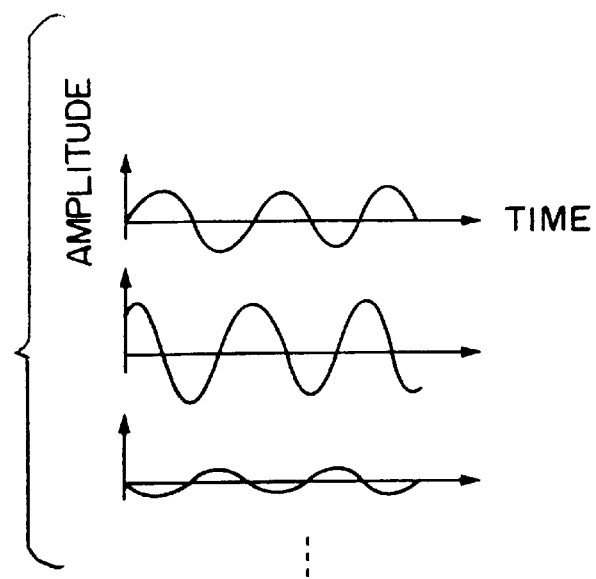
FIGS. 14A to 14C are explanatory views of a signal processing method in the signal processing circuit shown in FIG. 12.

In the same manner as described in the incoherent summation method with reference to FIGS. 3 and 4: the heterodyne signal outputs from the multiple detector elements 31 constituting the photo detector array 30 are given in the forms $$A_1 \sin (\Delta\omega t + \phi_1)$$

$$A_2 \sin (\Delta\omega t + \phi_2)$$

$$A_3 \sin (\Delta\omega t + \phi_3)$$

where $\Delta\omega = 2\pi\Delta f$ denotes a difference in angular frequencies between the signal light and the reference light, $A_1, A_1, A_3, \ldots$ are amplitudes of respective heterodyne signals, and $\phi_1, \phi_2, \phi_3, \ldots$ are phases of heterodyne signals. Generally the amplitudes $A_1, A_2, A_3, \ldots$ and the phases $\phi_1, \phi_2, \phi_3, \ldots$, as shown in FIG. 14A, differ from one another.

Figure 14B:
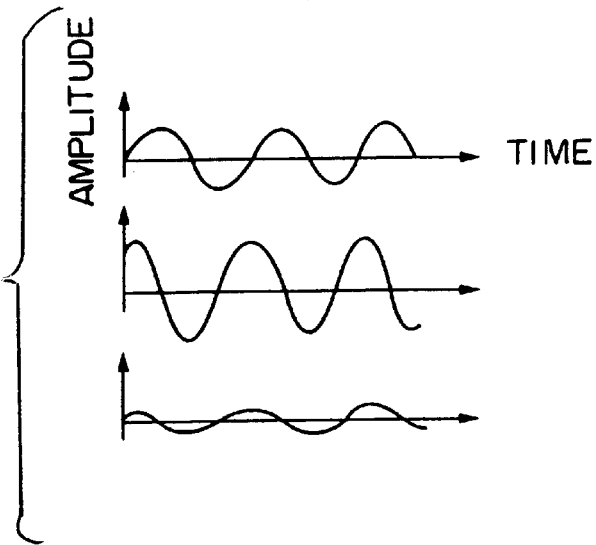

The signal processing circuit 400 shown in FIG. 12 is, as shown in FIG. 13, equipped with a phase matching circuit 411 and a summation circuit 412. Heterodyne signals $A_1 \sin (\Delta\omega t + \phi_1)$, $A_2 \sin (\Delta\omega t + \phi_2)$, $A_3 \sin (\Delta\omega t + \phi_3)$, from the detector elements 31 of the photo detector array 30 are transferred to the phase matching circuit 411, and, as shown in FIG. 14B, they are phase matched to, for example, the phase of the heterodyne signal from the detector element located in the center of the photo detector array 30. Then, $A_1 \sin (\Delta\omega t + \phi)$, $A_2 \sin (\Delta\omega t + \phi)$, $A_3 \sin (\Delta\omega t + \phi)$, . . . are obtained.

Figure 14C:
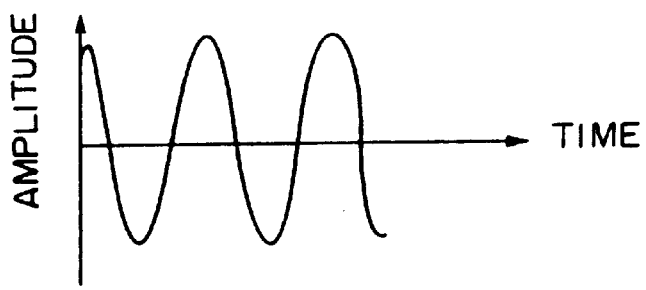

The summation circuit 412 sums up the phase-matched heterodyne signals, so that a signal $S = \Sigma A_n \cdot \sin (\Delta\omega t + \phi)$ shown in FIG. 14C is obtained.

In this manner, the signal $S = \Sigma A_n \sin (\Delta\omega t + \phi)$ from the processing circuit 400 in FIG. 12 is transferred to a velocity arithmetic circuit 410 for the calculation of fluid velocity.

In the signal processing circuit 400 shown in FIG. 12, that is, the phase matching circuit 411 and the summation circuit 412 shown in FIG. 13, the information regarding changes in phases with time or the phase information on the spatially different concerned points are not lost. Therefore, the present constitution 400 is suitable, for example, for the preprocessing in a laser Doppler velocimeter shown in FIG. 12.

As shown in FIG. 12, when the present invention is applied to a laser Doppler velocimeter, the amount of Doppler shift can be measured more precisely. As a result, the velocity can be obtained more accurately.

FIG. 15 is a schematic diagram of a fifth embodiment of the optical measurement device according to the present invention.

In the fifth embodiment shown in FIG. 15, an SLD (super luminescent diode) 51 as a light source having a low time coherence is used.

A light beam 51a emitted from the SLD 51 is collimated by lenses 12 and split into a signal light 51b and a reference light 51c by the beam splitter 13.

The signal light 51b separated from the reference light 51c by the beam splitter 13 is reflected by a mirror 52, transmitted through the sample 100 on the scanning stage 21, and transmitted via the lenses 22, 23 and 25 and the beam splitter 26 onto the photo detector array 30.

On the other hand, the reference light 51c separated from the signal light 51b by the beam splitter 13 is frequency shifted by the frequency shifter 17, total-reflected by a total reflection prism 53, reflected by a mirror 54, and has its beam diameter expanded by the beam expander 27. The reference lights are then superimposed on the signal lights via the beam splitter 26, and transmitted onto the photo detector array 30.

Heterodyne signal outputs from the detector elements 31 constituting the photo detector array 30 are transferred to the signal processing circuit 40 in which the aforementioned incoherent summation process is performed, before they are transferred to the computer 50.

Here, the total reflection prism 53 moves in a z direction shown by an arrow in FIG. 15 to vary the optical path length of the reference light 51c. Since the light beam 51a emitted from the SLD 51 has a low temporal coherence length, optical interference occurs only when the optical path length of the signal light is substantially equal to that of the reference light. Therefore, in the fifth embodiment, a high spatial resolution can be obtained in the optical axial direction. The present invention can be applied to such optical measurement.

Although a SLD 51 has been chosen for the description in the fifth embodiment shown in FIG. 15, a light emitting diode with a broad wavelength spectral band width may be used as well. Alternatively, it may use a femto-second pulsed laser which emits ultra-short laser with pulse width of the order of femto-seconds (one femto-second=$10^{-15}$ seconds). The spectral band width is in reverse proportion to a pulse width. The ultra-short pulsed laser has a broad wavelength spectrum, and, therefore, a low temporal coherence.

Figure 16:
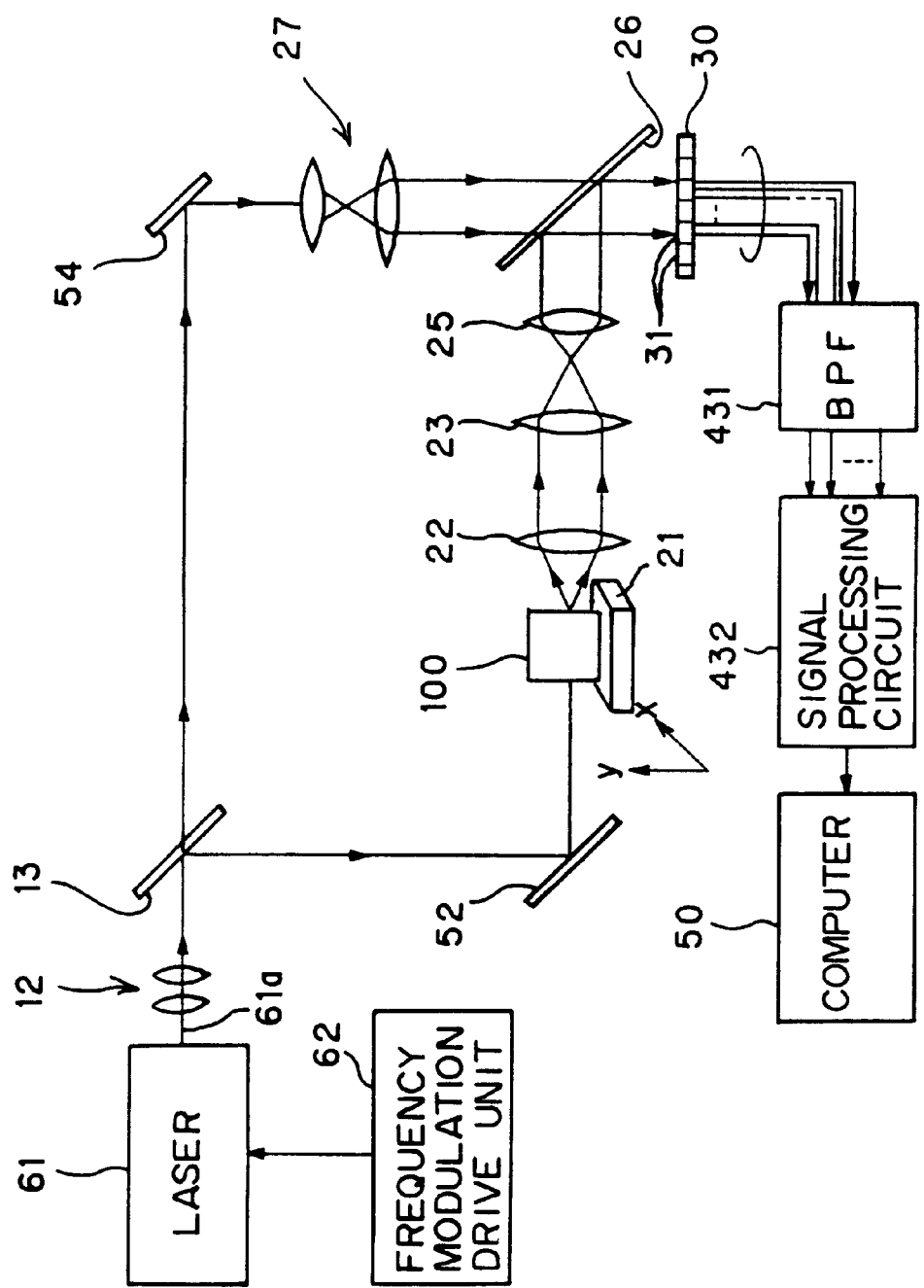
FIG. 16 is a schematic diagram of a sixth embodiment of the optical measurement device according to the present invention.

FIG. 16 is a schematic diagram of a sixth embodiment of the optical measurement device according to the present invention.

In the sixth embodiment shown in FIG. 16 used is a laser light source 61 which has a broad frequency modulation width. There is provided a frequency modulation drive unit 62 for modulating the frequency of a laser beam 61a which is emitted from the laser light source 61. Meanwhile, the frequency shifter 17 shown in FIG. 1 is not provided.

In the sixth embodiment according to the present invention, the frequency modulated laser is used as the light source. Therefore, the present invention can be applied to a so-called FM (frequency modulation) optical heterodyne detection method. For the FM optical heterodyne detection method itself, refer to, for example, Extended Abstract (The 58th Autumn Meeting, 1997); The Japan Society of Applied Physics, Paper No. 3p-L-1, page 954, by Koji Satori, Kin Pui Chan, and Humio Inaba.

The FM optical heterodyne detecting method is characterized in that by periodically modulating a laser optical frequency, heterodyne signal with a frequency proportional to the difference in optical path lengths between the signal light and the reference light can be obtained.

In the sixth embodiment shown in FIG. 16, heterodyne signals from by the detector elements 31 constituting the photo detector array 30 are first frequency filtered by a band pass filter 431. The band pass filter 431 is set to the frequency which equals the difference in optical path lengths between the signal light and the reference light. The heterodyne signals passed through the band pass filter 431 form signals each having the frequency that is equal to the difference in optical path lengths between the signal light and the reference light. In accordance with applications of the sixth embodiment shown in FIG. 16, a signal processing circuit 432 may perform at least one of the incoherent summation method (FIGS. 3 and 4) and the coherent summation method (FIG. 13 and 14). Also, by constituting the band pass filter 431 in such a manner that its central frequency can be freely changed, optical measurement with a high distance resolution can be realized.

As aforementioned, the present invention can be broadly applied to the field of measurements based on optical interference. Also, speckle noises can be averaged out while heterodyne signal intensity is also increased.

Figure 17:
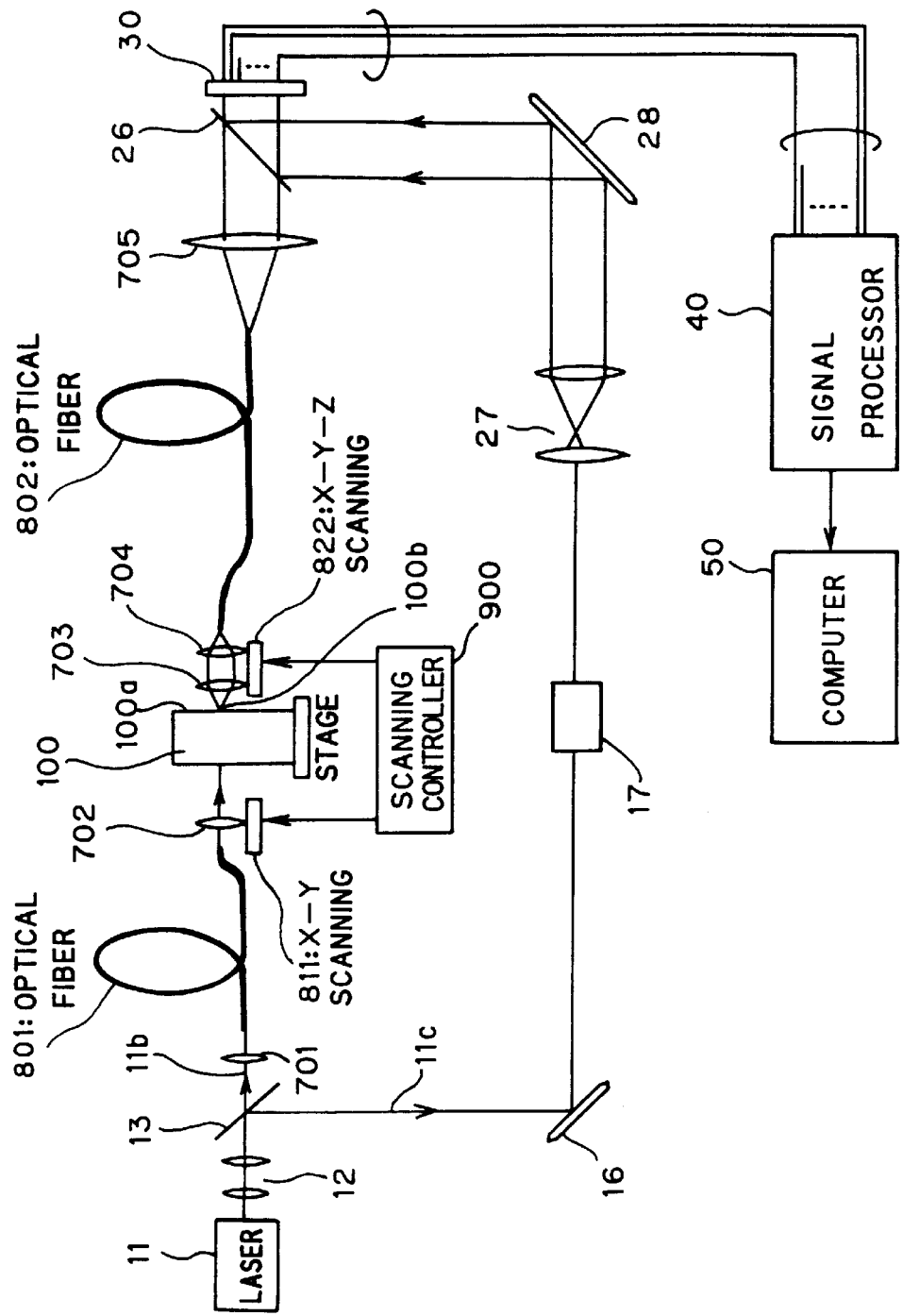
FIG. 17 is a schematic diagram of a seventh embodiment of the optical measurement device according to the present invention.

FIG. 17 is a schematic diagram of a seventh embodiment of the optical measurement device according to the present invention.

In the seventh embodiment shown in FIG. 17, an optical fiber 801 is used to guide the signal light to the sample 100, and another optical fiber 802 is used to collect the signal light transmitted through the sample 100 and also guides it to the photo detector array 30.

Here, the laser light beam emitted from a laser 11 is collimated by lenses 12 and split into a signal light 11b and a reference light 11c by the beam splitter 13.

The signal light separated from the reference beam by the beam splitter is coupled into an optical fiber 801 by a focusing lens 701, and waveguided by the optical fiber 801 to lens 702. The signal light coming out from the optical fiber 801 is collimated by lens 702, and then incident upon the sample 100.

The signal light transmitted through the sample 100 is collected and collimated by lens 703, and the collimated signal light is again coupled into an optical fiber 802 by a focusing lens 704, and waveguided to lens 705.

The signal light coming out from the optical fiber 802 is collimated by lens 705 to a beam diameter that is equal to or larger than the detection size of the photo detector array 30, and superimposed on the reference light via the beam splitter 26 for heterodyne detection using the photo detector array 30.

The use of optical fiber for the wave guide of the signal light in the seventh embodiment shown in FIG. 17 adds a high flexibility for guiding the signal light in the present invention. In FIG. 17, optical fiber 801 and lens 702 are both mounted on a scanning stage 811 which moves two-dimensionally in x and y directions, while optical fiber 802 and lenses 703 and 704 are mounted on another scanning stage 822 which moves three-dimensionally in x, y, and Z directions. By simultaneously scanning stage 811 and stage 822 in the same direction and at same speed, a two-dimensional scanning by means of scanning the incident beam instead of mechanically scanning the sample as shown in FIG. 1 can be achieved. A scanning controller 900 shown in FIG. 17 is for this simultaneous scanning purpose.

It is obvious that the stage on which the sample is mounted can be two-dimensionally scanned as well, in a same manner as that shown in FIG. 1, to obtain information on the sample.

The optical scanning method mentioned above will be particularly for the measurements where it is preferable not to move the sample, or the mechanical scanning of the stage on which the sample is mounted can not sustain the required high speed of scanning.

The use of a three-dimensional scanning stage 822 in FIG. 17 adds an additional advantage that by varying the distance between lens 703 and sample 100, the focal point of lens 703 can be on or underneath the surface 100a of sample 100. The result is that lens 703 can effectively collect the signal light emerging from either the concerned point 100b or from a concerned point that is underneath the surface 100a. This will be useful for the application of, for example, optical tomography.

What is claimed is:

1. An optical interferometer apparatus having spatially resolved detection capability to detect a spatially distorted wavefront of a light beam collected from a scattering media comprising:

a light source for emitting a light beam;

a beam splitter for splitting the light beam emitted from said light source into a first partial beam which is guided into an object arm of said optical interferometer apparatus and is then incident to a measured object which is disposed at a position along said object arm, and a second partial beam which is guided into a reference arm of said optical interferometer apparatus;

a collecting lens adapted for collecting light emerging from a point either on a surface of or an inside of said measured object to provide a signal light beam;

a recombining beam splitter for superimposing said signal light beam onto said second partial beam to provide a resultant interference light beam;

a photo detector array configuration having a plurality of spatially arranged detector elements to produce a plurality of detector signal outputs which are position sensitive to a wavefront and intensity distribution of said resultant interference light beam; and a signal processing unit for summing amplitudes of said plural detector signal outputs to produce a single point data having an amplitude that is regarded as being proportional to an intensity of said signal light beam collected from said point either on the surface of or the inside of said measured object.

2. The optical apparatus according to claim 1, wherein said object arm and said reference arm are parts of a Mach-Zehnder interferometer.

3. The optical apparatus according to claim 1, wherein said light source comprises a continuous wave laser.

4. The optical apparatus according to claim 1, wherein said light source comprises a continuous wave laser having a frequency that is periodically modulated.

5. The optical apparatus according to claim 1, wherein said light source comprises a light source having a short coherence length chosen from a group comprising a light emitting diode, a super luminescent diode, a femtosecond pulsed laser, and a gas discharge lamp.

6. The optical apparatus according to claim 1, wherein said light source comprises a pulsed laser.

7. The optical apparatus according to claim 1, further comprising a frequency difference imparting device for generating a frequency difference between the first partial light beam and the second partial light beam of said apparatus.

8. The optical apparatus according to claim 7, wherein said frequency difference imparting device comprises at least one or more acousto-optic modulators.

9. The optical apparatus according to claim 8, wherein said frequency difference imparting device comprises at least one or more electro-optic phase modulators.

10. The optical apparatus according to claim 8, wherein said frequency difference imparting device comprises a piezoelectric element.

11. The optical apparatus according the claim 1, further comprising a scanning mechanism which one-dimensionally or two-dimensionally moves at least one of the measured object and the first partial light beam in said object arm to scan said measured object with said first partial light beam.

12. The optical apparatus according to claim 1, further comprising a rotation mechanism that rotates at least one of the measured object and the first partial light beam in said object arm.

13. The optical apparatus according to claim 1, further comprising a pair of lenses disposed in the object arm for transmitting said signal light beam collected by said collecting lens to said recombining beam splitter, and an aperture disposed on a Fourier plane of the pair of lenses for spatial filtering.

14. The optical apparatus according to claim 1, wherein said signal processing unit rectifies and sums up said plurality of detector signal outputs from said photo detector array.

15. The optical apparatus according to claim 1, wherein said signal processing unit performs phase matching for said plural detector signal outputs from said photo detector array, and sums up their amplitudes.

* * * * *

Disclaimer 6,037,579—Kinpui Chan; Koji Satori, both of Yamagata, Japan. OPTICAL INTERFEROMETER EMPLOYING MULTIPLE DETECTORS TO DETECT SPATIALLY DISTORTED WAVEFRONT IN IMAGING OF SCATTERING MEDIA. Patent dated March 14, 2000. Disclaimer filed October 24, 2001, by the assignee, Biophotonics Information Laboratories LTD.

Hereby disclaims and dedicates to the Public all claims and entire term of said patent.
*(Official Gazette May 21, 2002)*